(12) United States Patent
Scheller

(10) Patent No.: US 10,022,267 B2
(45) Date of Patent: Jul. 17, 2018

(54) METHOD OF MANUFACTURING A MICROSURGICAL INSTRUMENT TIP

(71) Applicant: Katalyst Surgical, LLC, Chesterfield, MO (US)

(72) Inventor: Gregg D Scheller, Wildwood, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 623 days.

(21) Appl. No.: 14/657,270

(22) Filed: Mar. 13, 2015

(65) Prior Publication Data

US 2015/0297278 A1 Oct. 22, 2015

Related U.S. Application Data

(60) Provisional application No. 61/982,066, filed on Apr. 21, 2014.

(51) Int. Cl.
*A61B 17/29* (2006.01)
*A61F 9/007* (2006.01)
*A61B 17/00* (2006.01)
*A61B 17/30* (2006.01)

(52) U.S. Cl.
CPC .......... *A61F 9/00709* (2013.01); *A61B 17/29* (2013.01); *A61B 2017/00526* (2013.01); *A61B 2017/305* (2013.01); *Y10T 29/49789* (2015.01)

(58) Field of Classification Search
CPC ............... A61F 9/00709; A61B 17/29; A61B 2017/305; A61B 2017/00526; Y10T 29/49789; Y10T 29/49798
See application file for complete search history.

(56) References Cited

U.S. PATENT DOCUMENTS

| | | | | |
|---|---|---|---|---|
| 1,371,288 | A | * | 3/1921 | Wolhaupter ............. B21K 7/08 29/417 |
| 5,355,871 | A | | 10/1994 | Hurley et al. |
| 5,370,658 | A | | 12/1994 | Scheller et al. |
| 5,647,115 | A | * | 7/1997 | Slater ................. A61B 10/0266 29/557 |
| 5,893,873 | A | | 4/1999 | Rader et al. |
| 5,921,998 | A | | 7/1999 | Tano et al. |
| 6,488,695 | B1 | | 12/2002 | Hickingbotham |
| 6,575,989 | B1 | | 6/2003 | Scheller et al. |
| 6,730,076 | B2 | | 5/2004 | Hickingbotham |
| 6,772,765 | B2 | * | 8/2004 | Scheller ............. A61B 17/3201 128/898 |
| 6,863,668 | B2 | | 3/2005 | Gillespie et al. |
| 7,632,242 | B2 | | 12/2009 | Griffin et al. |

(Continued)

OTHER PUBLICATIONS

Steve Charles, Techniques and tools for dissection of epiretinal membranes, Graefe' Arch Clin Exp Ophthalmol, 241:347-352, 2003.

*Primary Examiner* — Sarang Afzali
(74) *Attorney, Agent, or Firm* — Kevin P. Rollins

(57) ABSTRACT

An assembled blank may include a blank tip attached to a blank base, e.g., the blank tip may be welded to the blank base. The blank tip may be manufactured by modifying flat stock, e.g., tiers of blank tips may be manufactured by modifying tiers of flat stock. The blank tip may comprise a first forceps jaw, a second forceps jaw, and a blank tip aperture. The assembled blank may be disposed within a hypodermic tube and an actuation structure of a microsurgical instrument.

19 Claims, 19 Drawing Sheets

(56) References Cited

U.S. PATENT DOCUMENTS

| | | |
|---|---|---|
| 7,766,904 B2 | 10/2010 | McGowan, Sr. et al. |
| 8,038,692 B2 | 10/2011 | Valencia et al. |
| 8,197,468 B2 | 6/2012 | Scheller et al. |
| 2003/0171762 A1 | 9/2003 | Forchette et al. |
| 2005/0154403 A1 | 7/2005 | Sauer et al. |
| 2006/0235382 A1 | 10/2006 | Cohen et al. |
| 2007/0185514 A1 | 8/2007 | Kirchhevel |
| 2007/0282348 A1 | 12/2007 | Lumpkin |
| 2008/0183199 A1 | 7/2008 | Attinger |
| 2009/0228066 A1 | 10/2009 | Hirata et al. |
| 2012/0116361 A1 | 5/2012 | Hanlon et al. |
| 2013/0085326 A1 | 4/2013 | Scheller et al. |
| 2013/0197488 A1 | 8/2013 | Scheller et al. |
| 2014/0066977 A1 | 3/2014 | Scheller et al. |
| 2014/0121697 A1 | 5/2014 | Scheller et al. |
| 2014/0128909 A1 | 5/2014 | Scheller et al. |
| 2014/0142603 A1 | 5/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |

* cited by examiner

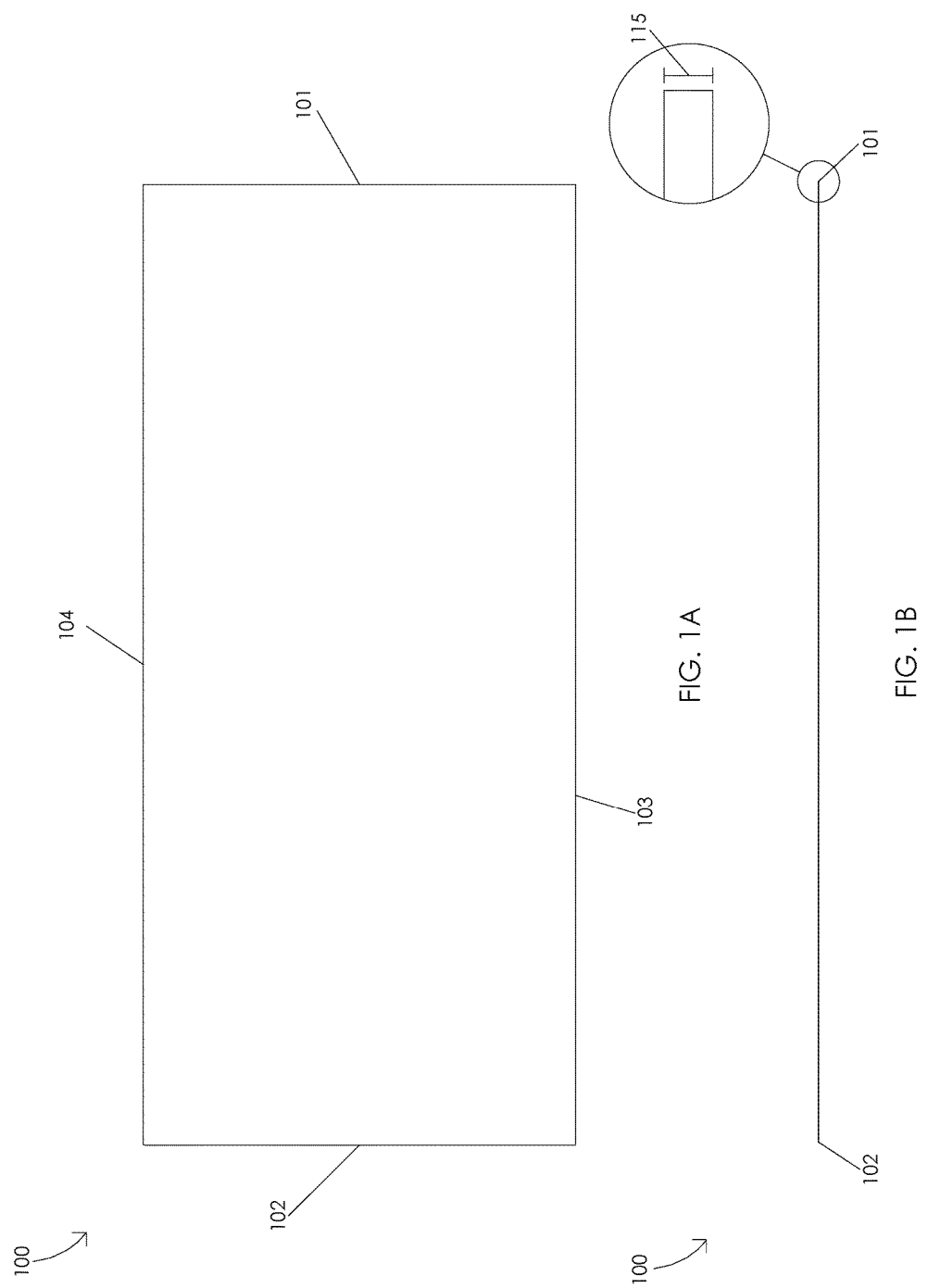

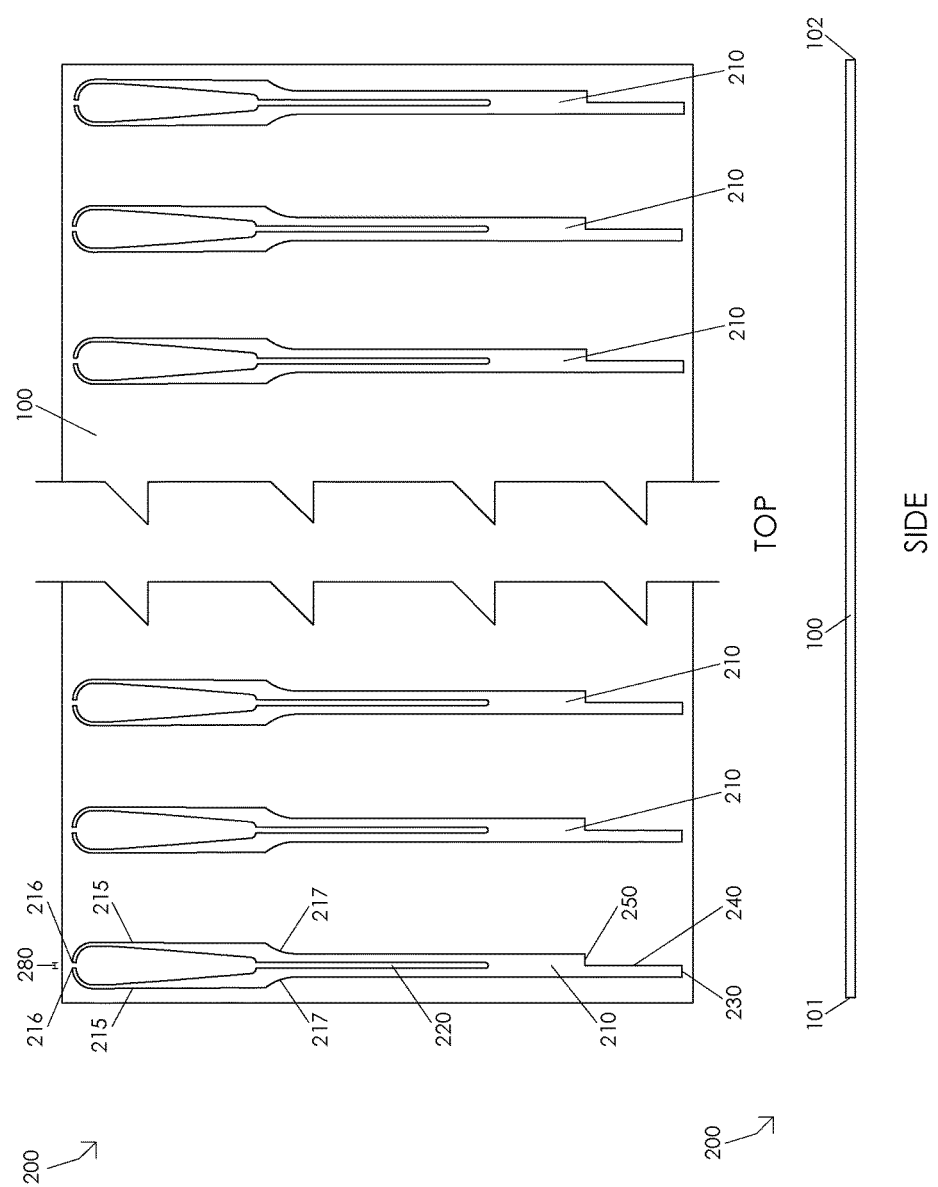

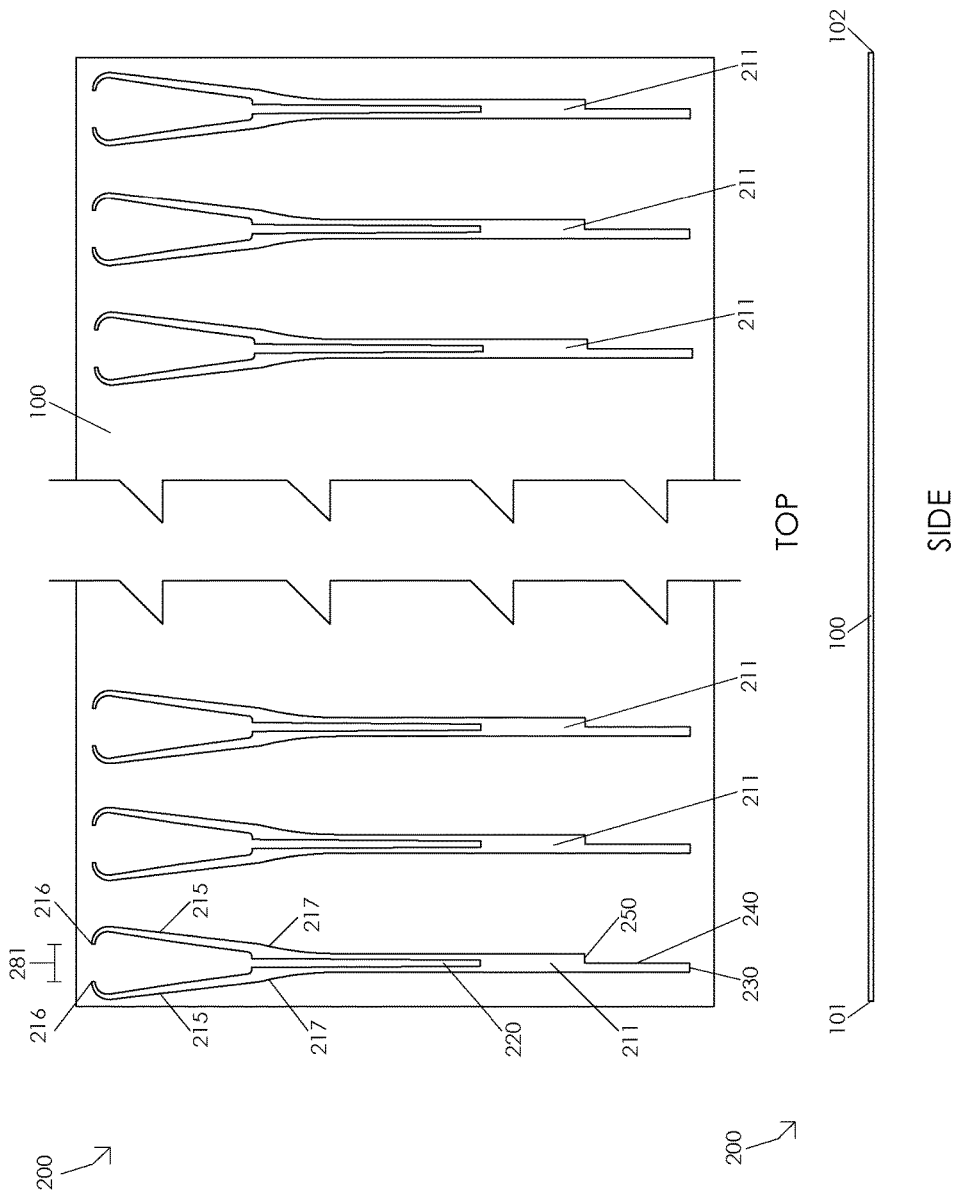

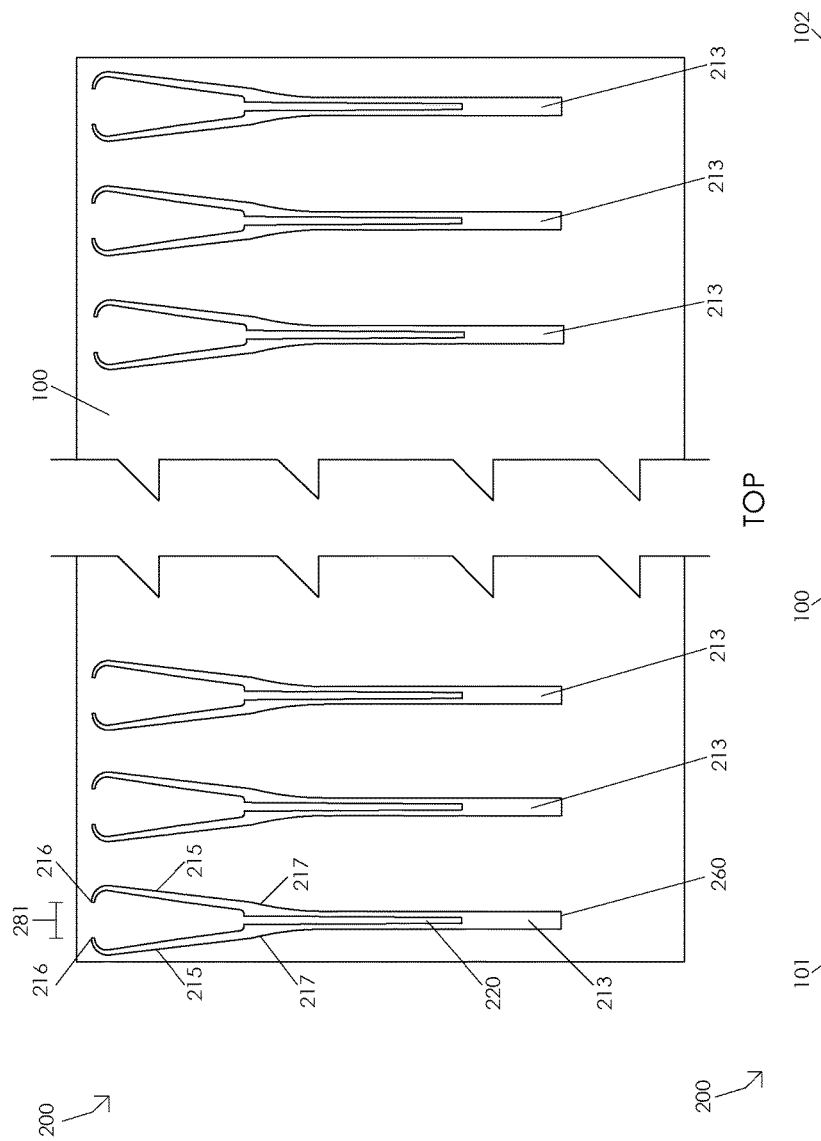

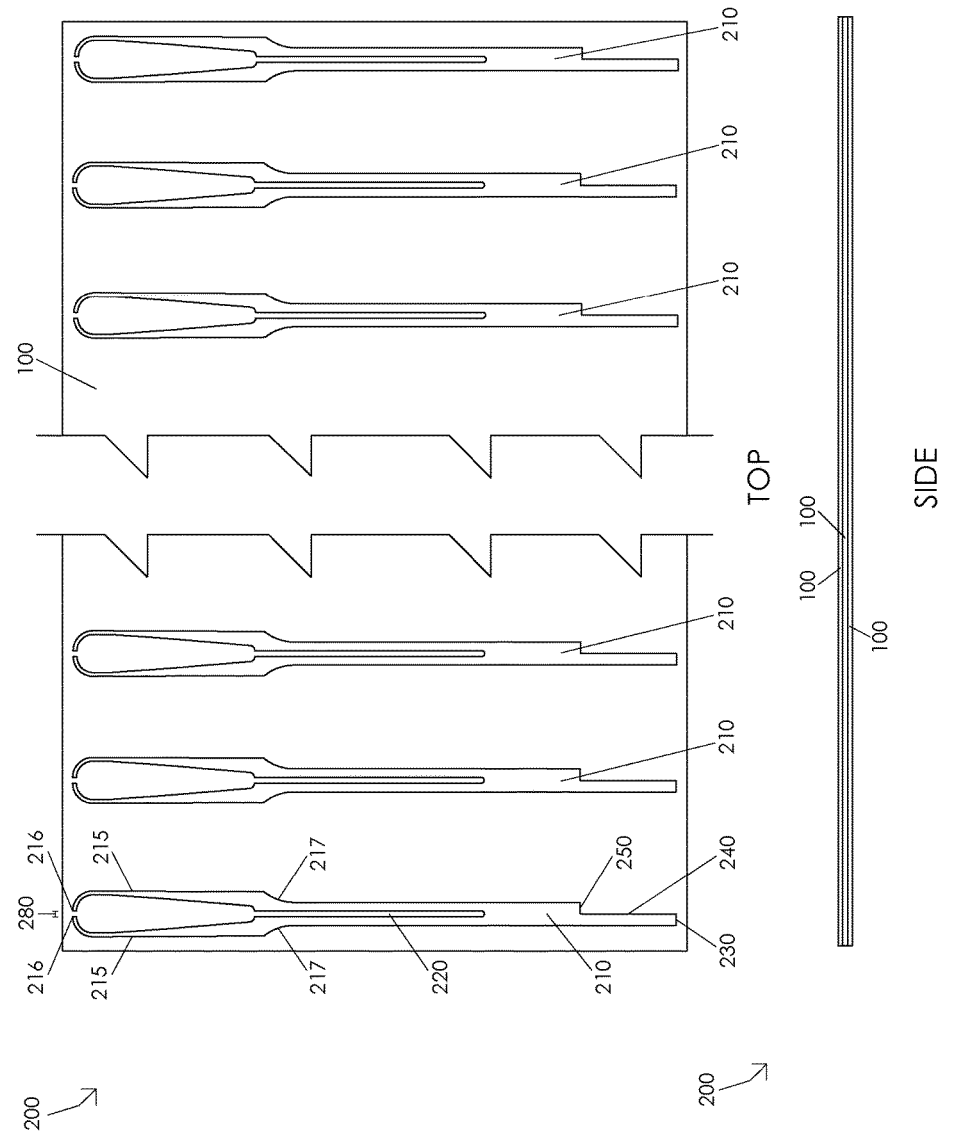

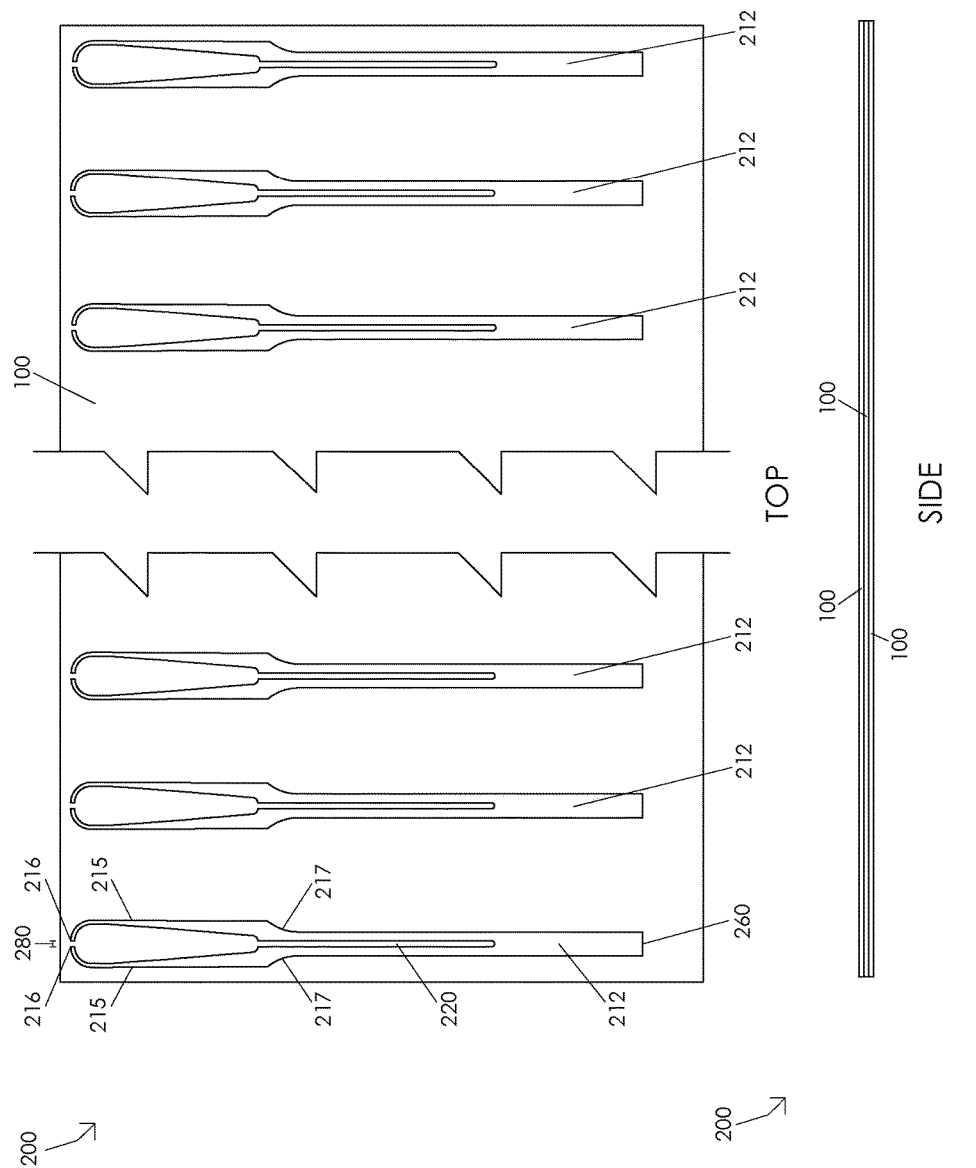

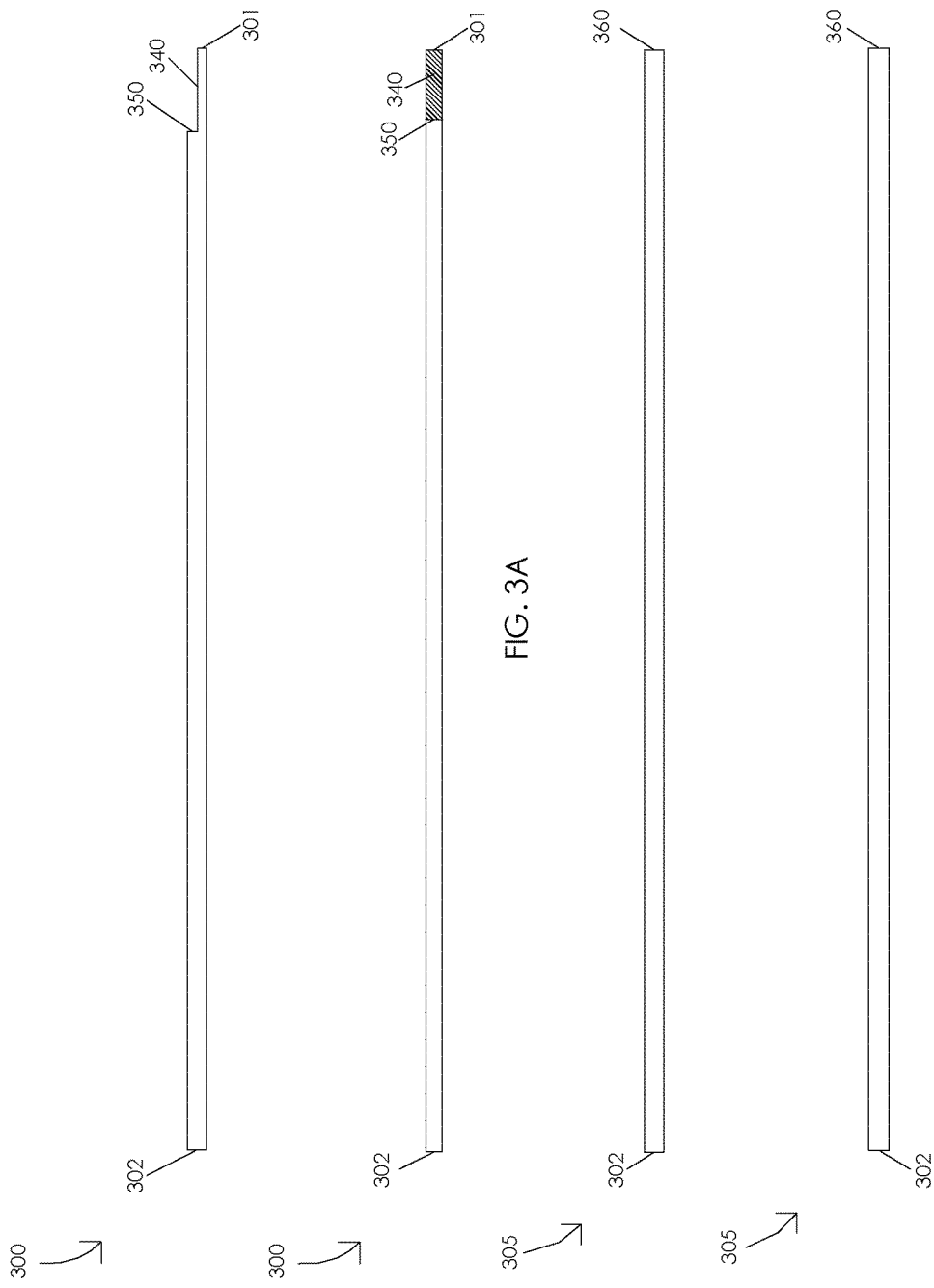

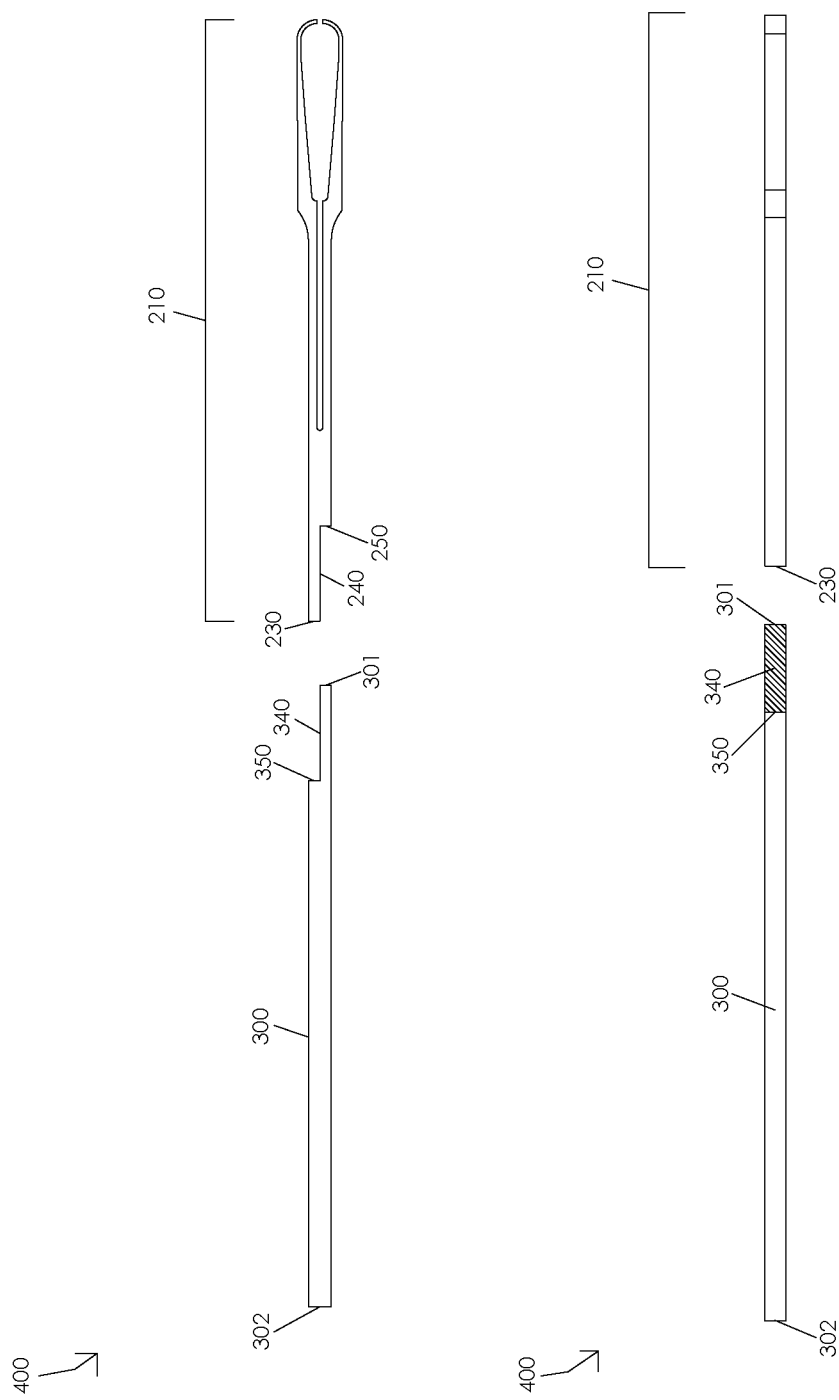

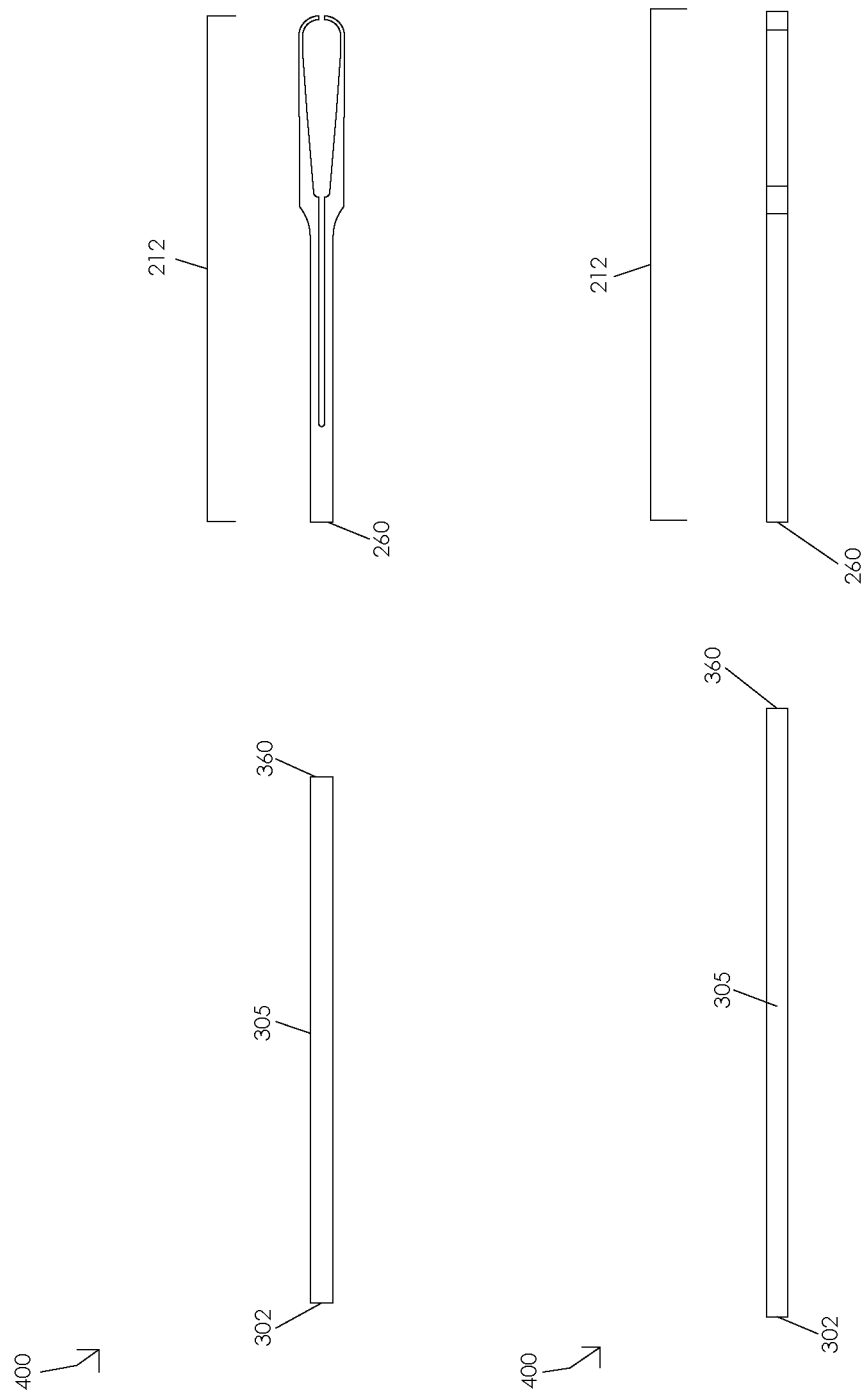

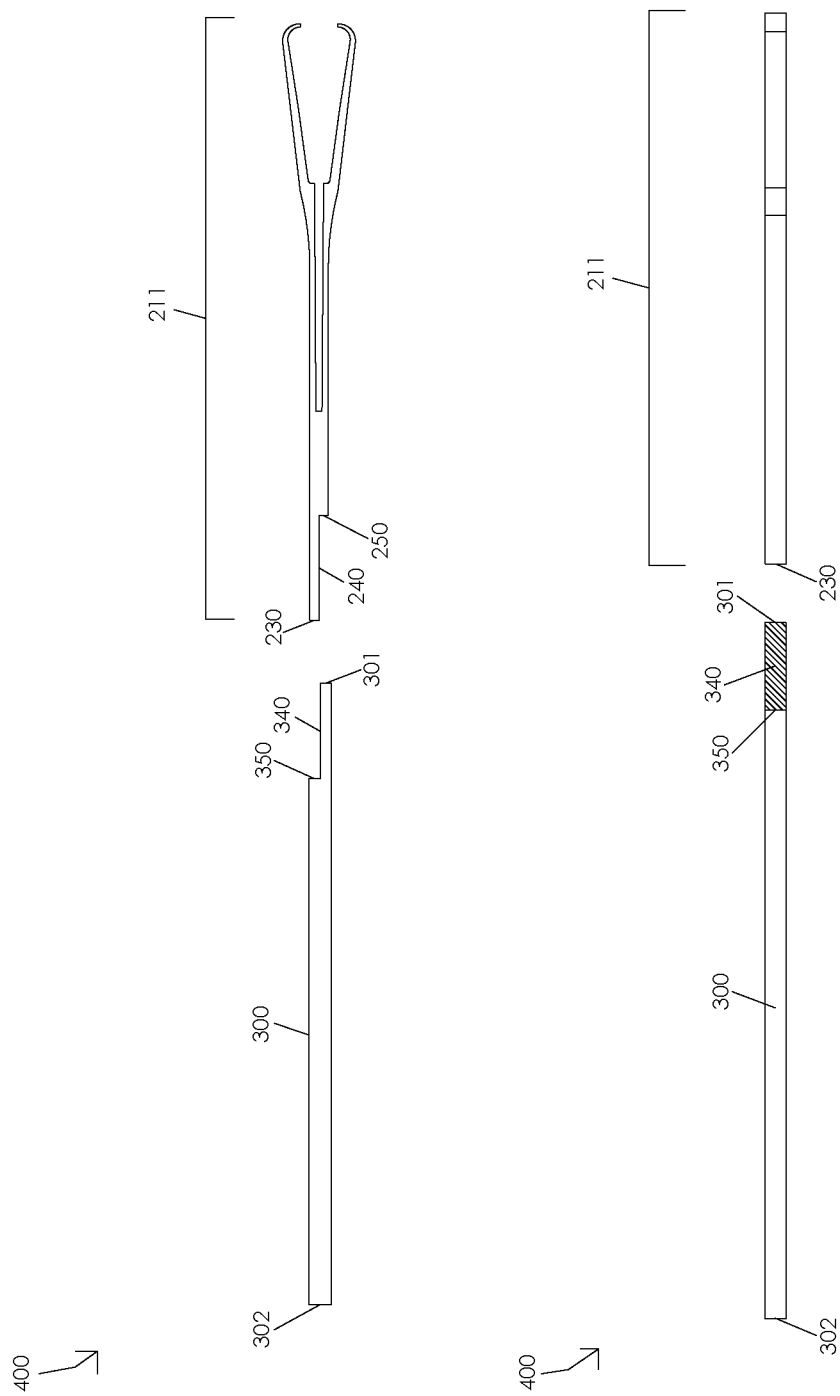

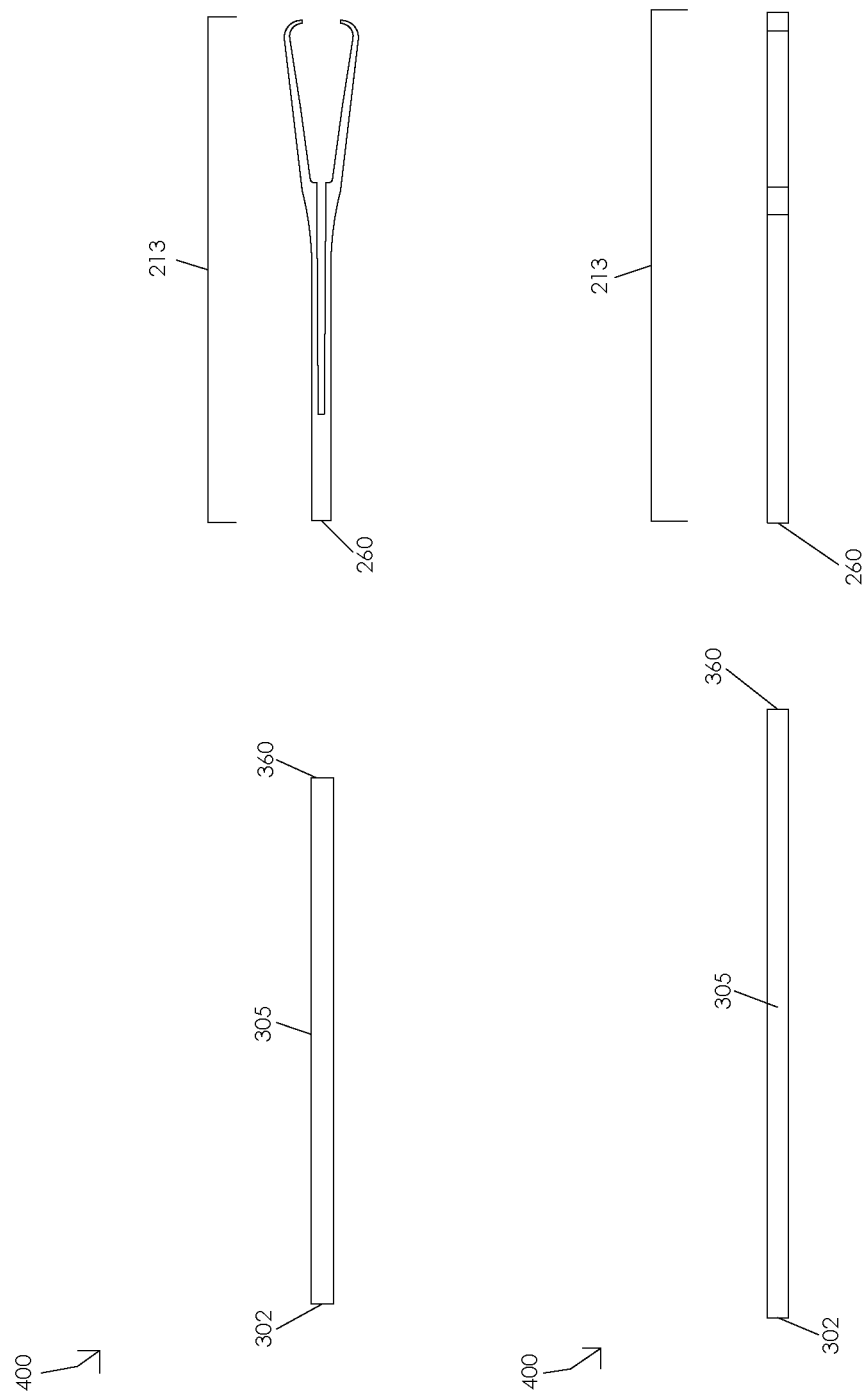

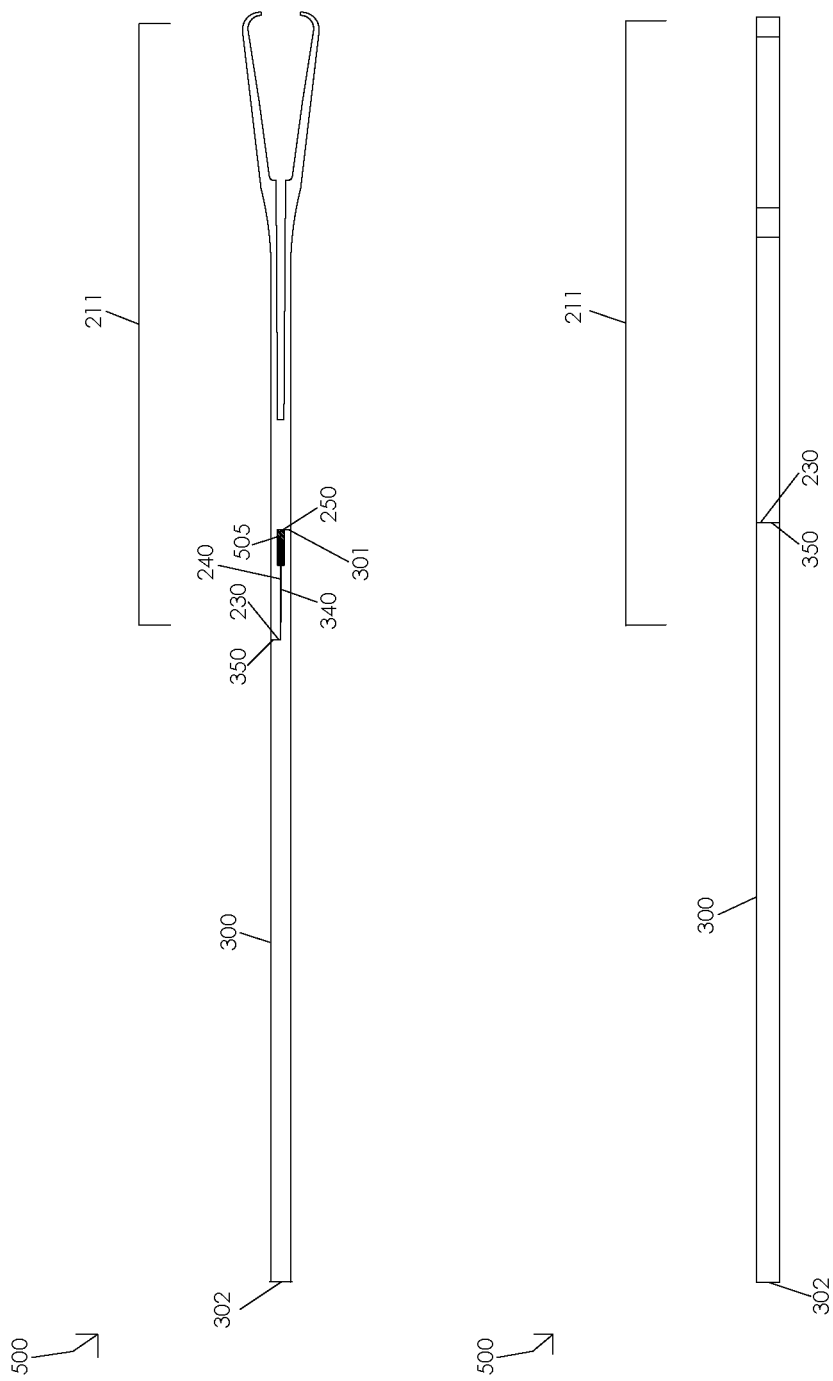

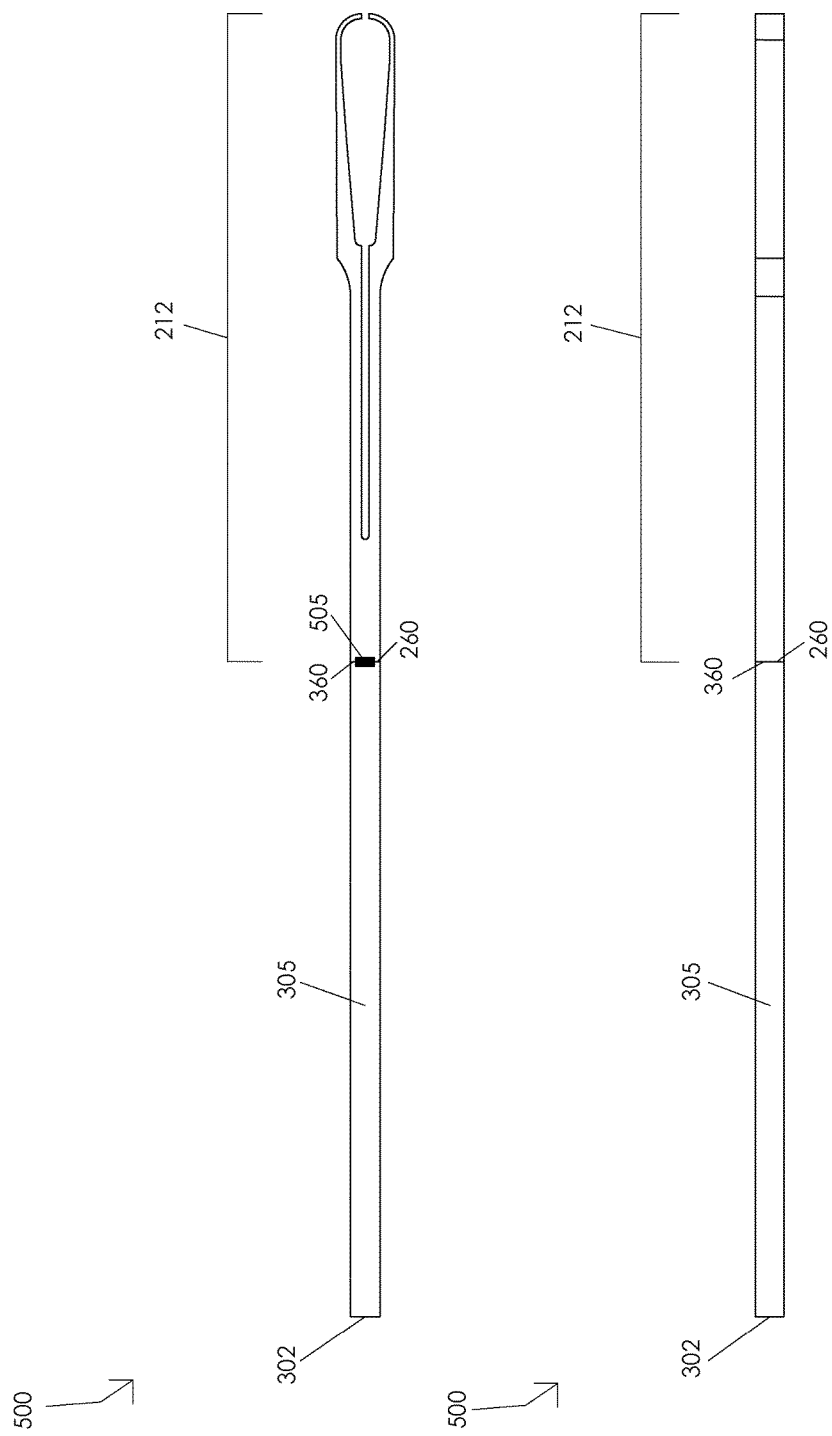

METHOD OF MANUFACTURING A MICROSURGICAL INSTRUMENT TIP

CROSS-REFERENCE TO RELATED APPLICATIONS

This application claims the benefit of U.S. Provisional Application No. 61/982,066, filed Apr. 21, 2014.

FIELD OF THE INVENTION

The present disclosure relates to a surgical instrument, and, more particularly, to a microsurgical instrument tip.

BACKGROUND OF THE INVENTION

Microsurgical instrument tips are commonly manufactured from metal blanks A metal blank is a thin, elongate wire having a block portion at one end. Metal blanks are typically custom manufactured by a first specialized machinist operating a first piece of capital equipment, e.g., a CNC machinist operating a Swiss-style lathe. After a metal blank is manufactured, the metal blank is modified by a second specialized machinist operating a second piece of capital equipment, e.g., an EDM machinist operating an electrical discharge machine. Metal blanks are modified into microsurgical instrument tips one metal blank at a time, e.g., an EDM machinist operating an electrical discharge machine manufactures a first microsurgical instrument tip from a first metal blank and then the EDM machinist manufactures a second microsurgical instrument tip from a second metal blank.

BRIEF SUMMARY OF THE INVENTION

In one or more embodiments, an assembled blank may comprise a blank tip attached to a blank base, e.g., the blank tip may be welded to the blank base. Illustratively, the blank tip may be manufactured by modifying flat stock, e.g., tiers of blank tips may be manufactured by modifying tiers of flat stock. In one or more embodiments, the blank tip may comprise a first forceps jaw, a second forceps jaw, and a blank tip aperture. Illustratively, the assembled blank may be disposed within a hypodermic tube and an actuation structure of a microsurgical instrument.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a flat stock;

FIGS. 2A, 2B, 2C, 2D, 2E, 2F, 2G and 2H are schematic diagrams illustrating a modified flat stock;

FIGS. 3A and 3B are schematic diagrams illustrating a blank base;

FIGS. 4A, 4B, 4C, and 4D are schematic diagrams illustrating exploded views of a blank assembly;

FIGS. 5A, 5B, 5C, and 5D are schematic diagrams illustrating an assembled blank;

DETAILED DESCRIPTION OF AN ILLUSTRATIVE EMBODIMENT

Figure 2B:
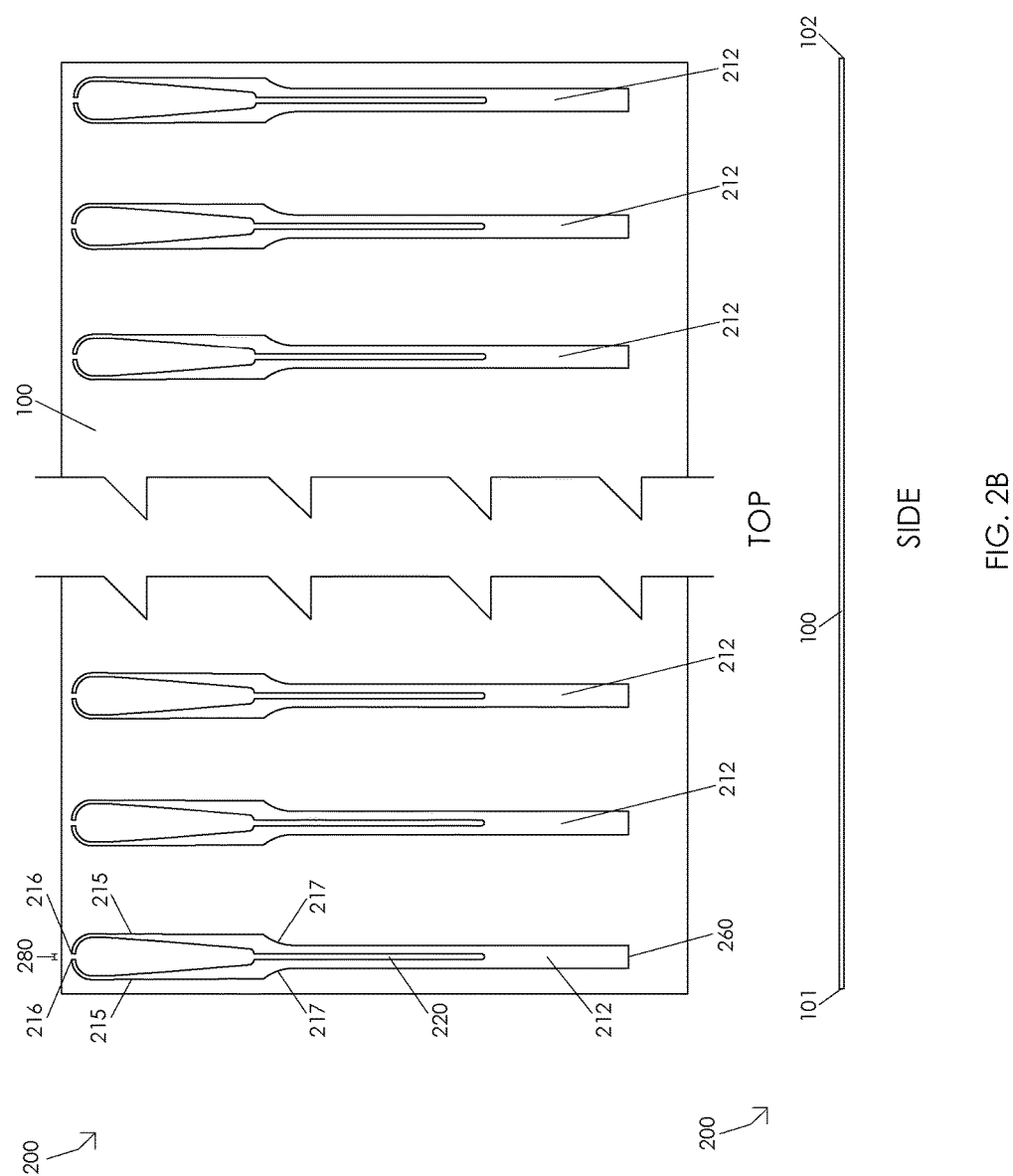

FIGS. 1A and 1B are schematic diagrams illustrating a flat stock 100. FIG. 1A illustrates a top view of flat stock 100. Illustratively, flat stock 100 may comprise a flat stock distal end 101, a flat stock proximal end 102, a flat stock dorsal end 103, and a flat stock ventral end 104. FIG. 1B illustrates a side view of flat stock 100. In one or more embodiments, flat stock 100 may comprise a flat stock thickness 115. Illustratively, flat stock thickness 115 may be a distance in a range of 0.005 to 0.013 inches, e.g., flat stock thickness 115 may be a distance of 0.008 inches. In one or more embodiments, flat stock thickness 115 may be a distance of less than 0.005 inches or greater than 0.013 inches. Illustratively, flat stock thickness 115 may be a specific distance corresponding to a particular size of microsurgical instrument. In one or more embodiments, flat stock thickness 115 may be a distance in a range of 0.007 to 0.009 inches for a 25 gauge ophthalmic surgical forceps, e.g., flat stock thickness 115 may be a distance of 0.008 inches for a 25 gauge ophthalmic surgical forceps. Illustratively, flat stock thickness 115 may be a distance in a range of 0.011 to 0.013 inches for a 23 gauge ophthalmic surgical forceps, e.g., flat stock thickness 115 may be a distance of 0.012 inches for a 23 gauge ophthalmic surgical forceps. In one or more embodiments, flat stock 100 may be manufactured from any suitable material, e.g., polymers, metals, metal alloys, etc., or from any combination of suitable materials. Illustratively, flat stock 100 may be manufactured from stainless steel, e.g., flat stock 100 may be manufactured from 17-7 PH Stainless Steel Condition C.

FIGS. 2A, 2B, 2C, 2D, 2E, 2F, 2G and 2H are schematic diagrams illustrating a modified flat stock 200. FIG. 2A illustrates modified flat stock 200 to manufacture a closed step blank tip 210. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of closed step blank tips 210, e.g., flat stock 100 may be actuated relative to a tool electrode of an electrical discharge machine to cut out a plurality of closed step blank tips 210. For example, flat stock 100 may be disposed in a plane perpendicular to a tool electrode of an electrical discharge machine and then flat stock 100 may be actuated relative to the tool electrode to cut out a plurality of closed step blank tips 210. Illustratively, closed step blank tip 210 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, a blank base shoulder interface 230, a blank base interface 240, and a blank tip shoulder 250. In one or more embodiments, first forceps jaw distal end 216 and second forceps jaw distal end 216 may be separated by a closed jaw separation distance 280. Illustratively, closed jaw separation distance 280 may be a distance in a range of 0.001 to 0.005 inches, e.g., closed jaw separation distance 280 may be a distance of 0.003 inches. In one or more embodiments, closed jaw separation distance 280 may be a distance of less than 0.001 inches or greater than 0.005 inches.

FIG. 2B illustrates modified flat stock 200 to manufacture a closed blunt blank tip 212. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of closed blunt blank tips 212, e.g., flat stock 100 may be actuated relative to a tool electrode of an electrical discharge machine to cut out a plurality of closed blunt blank tips 212. For example, flat stock 100 may be disposed in a plane perpendicular to a tool electrode of an electrical discharge machine and then flat stock 100 may be actuated relative to the tool electrode to cut out a plurality of closed blunt blank tips 212. Illustratively, closed blunt blank tip 212 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, and a blunt blank base interface 260. In one or more embodiments, first forceps jaw distal end 216 and second forceps jaw distal end 216 may be separated by a closed jaw separation distance 280. Illustratively, closed jaw separation distance 280 may be a distance in a range of 0.001 to 0.005 inches, e.g., closed jaw separation distance 280 may be a distance of 0.003 inches. In one or more embodiments, closed jaw separation distance 280 may be a distance of less than 0.001 inches or greater than 0.005 inches.

FIG. 2C illustrates modified flat stock 200 to manufacture an open step blank tip 211. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of open step blank tips 211, e.g., flat stock 100 may be actuated relative to a tool electrode of an electrical discharge machine to cut out a plurality of open step blank tips 211. For example, flat stock 100 may be disposed in a plane perpendicular to a tool electrode of an electrical discharge machine and then flat stock 100 may be actuated relative to the tool electrode to cut out a plurality of open step blank tips 211. Illustratively, open step blank tip 211 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, a blank base shoulder interface 230, a blank base interface 240, and a blank tip shoulder 250. In one or more embodiments, first forceps jaw distal end 216 and second forceps jaw distal end 216 may be separated by an open jaw separation distance 281. Illustratively, open jaw separation distance 281 may be a distance in a range of 0.010 to 0.050 inches, e.g., open jaw separation distance 281 may be a distance of 0.038 inches. In one or more embodiments, open jaw separation distance 281 may be a distance of less than 0.010 inches or greater than 0.050 inches. Illustratively, open jaw separation distance 181 may be a specific distance corresponding to a particular size of microsurgical instrument. In one or more embodiments, open jaw separation distance 181 may be a distance in a range of 0.025 to 0.035 inches for a 25 gauge ophthalmic surgical forceps, e.g., open jaw separation distance 181 may be a distance of 0.030 inches for a 25 gauge ophthalmic surgical forceps. Illustratively, open jaw separation distance 181 may be a distance in a range of 0.030 to 0.045 inches for a 23 gauge ophthalmic surgical forceps, e.g., open jaw separation distance 181 may be a distance of 0.038 inches for a 23 gauge ophthalmic surgical forceps.

FIG. 2D illustrates modified flat stock 200 to manufacture an open blunt blank tip 213. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of open blunt blank tips 213, e.g., flat stock 100 may be actuated relative to a tool electrode of an electrical discharge machine to cut out a plurality of open blunt blank tips 213. For example, flat stock 100 may be disposed in a plane perpendicular to a tool electrode of an electrical discharge machine and then flat stock 100 may be actuated relative to the tool electrode to cut out a plurality of open blunt blank tips 213. Illustratively, open blunt blank tip 213 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, and a blunt blank base interface 260. In one or more embodiments, first forceps jaw distal end 216 and second forceps jaw distal end 216 may be separated by an open jaw separation distance 281. Illustratively, open jaw separation distance 281 may be a distance in a range of 0.010 to 0.050 inches, e.g., open jaw separation distance 281 may be a distance of 0.038 inches. In one or more embodiments, open jaw separation distance 281 may be a distance of less than 0.010 inches or greater than 0.050 inches. Illustratively, open jaw separation distance 181 may be a specific distance corresponding to a particular size of microsurgical instrument. In one or more embodiments, open jaw separation distance 181 may be a distance in a range of 0.025 to 0.035 inches for a 25 gauge ophthalmic surgical forceps, e.g., open jaw separation distance 181 may be a distance of 0.030 inches for a 25 gauge ophthalmic surgical forceps. Illustratively, open jaw separation distance 181 may be a distance in a range of 0.030 to 0.045 inches for a 23 gauge ophthalmic surgical forceps, e.g., open jaw separation distance 181 may be a distance of 0.038 inches for a 23 gauge ophthalmic surgical forceps.

FIG. 2E illustrates modified flat stock 200 to manufacture a plurality of closed step blank tips 210 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of closed step blank tips 210, e.g., tiers of flat stock 100 may be actuated relative to a tool electrode of an electrical discharge machine to cut out a plurality of tiers of closed step blank tips 210. For example, tiers of flat stock 100 may be disposed in a plane perpendicular to a tool electrode of an electrical discharge machine and then tiers of flat stock 100 may be actuated relative to the tool electrode to cut out a plurality of closed step blank tips 210.

FIG. 2F illustrates modified flat stock 200 to manufacture a plurality of closed blunt blank tips 212 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of closed blunt blank tips 212, e.g., tiers of flat stock 100 may be actuated relative to a tool electrode of an electrical discharge machine to cut out a plurality of tiers of closed blunt blank tips 212. For example, tiers of flat stock 100 may be disposed in a plane perpendicular to a tool electrode of an electrical discharge machine and then tiers of flat stock 100 may be actuated relative to the tool electrode to cut out a plurality of closed blunt blank tips 212.

Figure 2G:
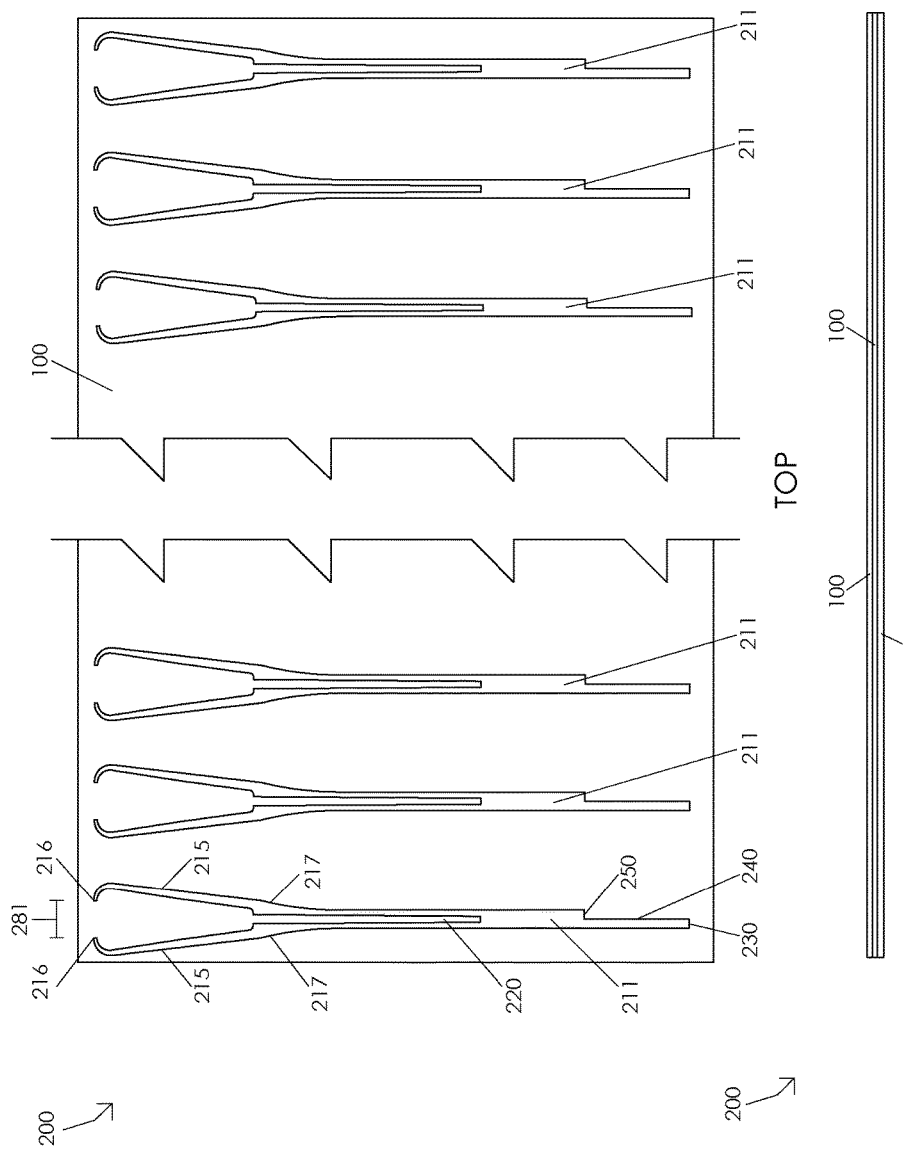

FIG. 2G illustrates modified flat stock 200 to manufacture a plurality of open step blank tips 211 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of open step blank tips 211, e.g., tiers of flat stock 100 may be actuated relative to a tool electrode of an electrical discharge machine to cut out a plurality of tiers of open step blank tips 211. For example, tiers of flat stock 100 may be disposed in a plane perpendicular to a tool electrode of an electrical discharge machine and then tiers of flat stock 100 may be actuated relative to the tool electrode to cut out a plurality of open step blank tips 211.

Figure 2H:
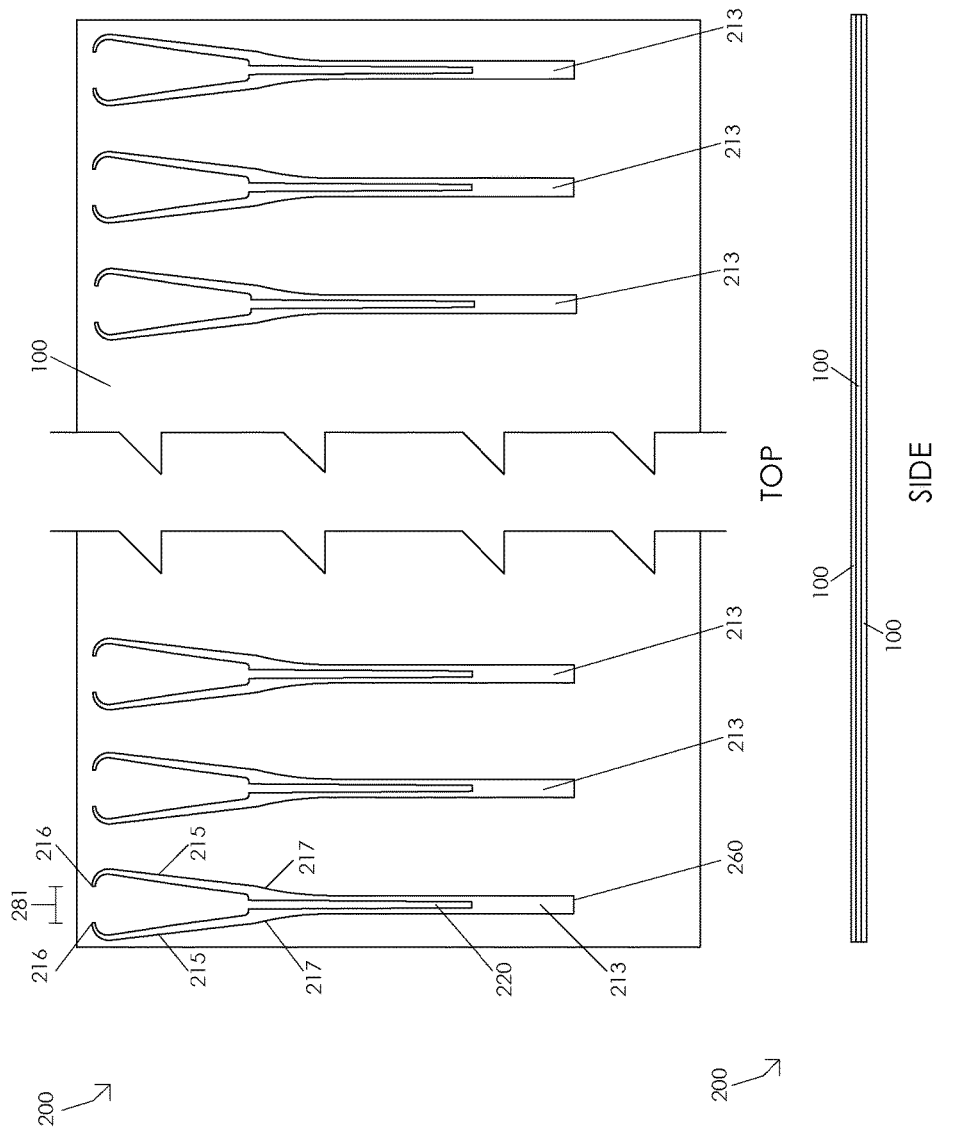

FIG. 2H illustrates modified flat stock 200 to manufacture a plurality of open blunt blank tips 213 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of open blunt blank tips 213, e.g., tiers of flat stock 100 may be actuated relative to a tool electrode of an electrical discharge machine to cut out a plurality of tiers of open blunt blank tips 213. For example, tiers of flat stock 100 may be disposed in a plane perpendicular to a tool electrode of an electrical discharge machine and then tiers of flat stock 100 may be actuated relative to the tool electrode to cut out a plurality of open blunt blank tips 213.

FIGS. 3A and 3B are schematic diagrams illustrating a blank base. FIG. 3A illustrates a top view and a side view of a step blank base 300. Illustratively, step blank base 300 may comprise a blank tip shoulder interface 301, a blank proximal end 302, a blank tip interface 340, and a blank base shoulder 350. In one or more embodiments, step blank base 300 may be manufactured from any suitable material, e.g., polymers, metals, metal alloys, etc., or from any combination of suitable materials. Illustratively, step blank base 300 may be manufactured from stainless steel, e.g., step blank base 300 may be manufactured from 17-7 PH Stainless Steel Condition C. FIG. 3B illustrates a top view and a side view of a blunt blank base 305. Illustratively, blunt blank base 305 may comprise a blank proximal end 302 and a blunt blank tip interface 360. In one or more embodiments, blunt blank base 305 may be manufactured from any suitable material, e.g., polymers, metals, metal alloys, etc., or from any combination of suitable materials. Illustratively, blunt blank base 305 may be manufactured from stainless steel, e.g., blunt blank base 305 may be manufactured from 17-7 PH Stainless Steel Condition C.

FIGS. 4A, 4B, 4C, and 4D are schematic diagrams illustrating exploded views of a blank assembly 400. FIG. 4A illustrates a top view and a side view of a blank assembly 400. In one or more embodiments, blank assembly 400 may comprise a step blank base 300 and a closed step blank tip 210. Illustratively, a portion of step blank base 300 may be configured to interface with a portion of closed step blank tip 210, e.g., a portion of closed step blank tip 210 may be configured to interface with a portion of step blank base 300. In one or more embodiments, closed step blank tip 210 and step blank base 300 may be disposed wherein blank base shoulder interface 230 abuts blank base shoulder 350. Illustratively, closed step blank tip 210 and step blank base 300 may be disposed wherein blank tip shoulder 250 abuts blank tip shoulder interface 301. In one or more embodiments, closed step blank tip 210 and step blank base 300 may be disposed wherein blank base interface 240 abuts blank tip interface 340.

FIG. 4B illustrates a top view and a side view of a blank assembly 400. In one or more embodiments, blank assembly 400 may comprise a blunt blank base 305 and a closed blunt blank tip 212. Illustratively, a portion of blunt blank base 305 may be configured to interface with a portion of closed blunt blank tip 212, e.g., a portion of closed blunt blank tip 212 may be configured to interface with a portion of blunt blank base 305. In one or more embodiments, closed blunt blank tip 212 and blunt blank base 305 may be disposed wherein blunt blank base interface 260 abuts blunt blank tip interface 360.

FIG. 4C illustrates a top view and a side view of a blank assembly 400. In one or more embodiments, blank assembly 400 may comprise a step blank base 300 and an open step blank tip 211. Illustratively, a portion of step blank base 300 may be configured to interface with a portion of open step blank tip 211, e.g., a portion of open step blank tip 211 may be configured to interface with a portion of step blank base 300. In one or more embodiments, open step blank tip 211 and step blank base 300 may be disposed wherein blank base shoulder interface 230 abuts blank base shoulder 350. Illustratively, open step blank tip 211 and step blank base 300 may be disposed wherein blank tip shoulder 250 abuts blank tip shoulder interface 301. In one or more embodiments, open step blank tip 210 and step blank base 300 may be disposed wherein blank base interface 240 abuts blank tip interface 340.

FIG. 4D illustrates a top view and a side view of a blank assembly 400. In one or more embodiments, blank assembly 400 may comprise a blunt blank base 305 and an open blunt blank tip 213. Illustratively, a portion of blunt blank base 305 may be configured to interface with a portion of open blunt blank tip 213, e.g., a portion of open blunt blank tip 213 may be configured to interface with a portion of blunt blank base 305. In one or more embodiments, open blunt blank tip 213 and blunt blank base 305 may be disposed wherein blunt blank base interface 260 abuts blunt blank tip interface 360.

Figure 5A:
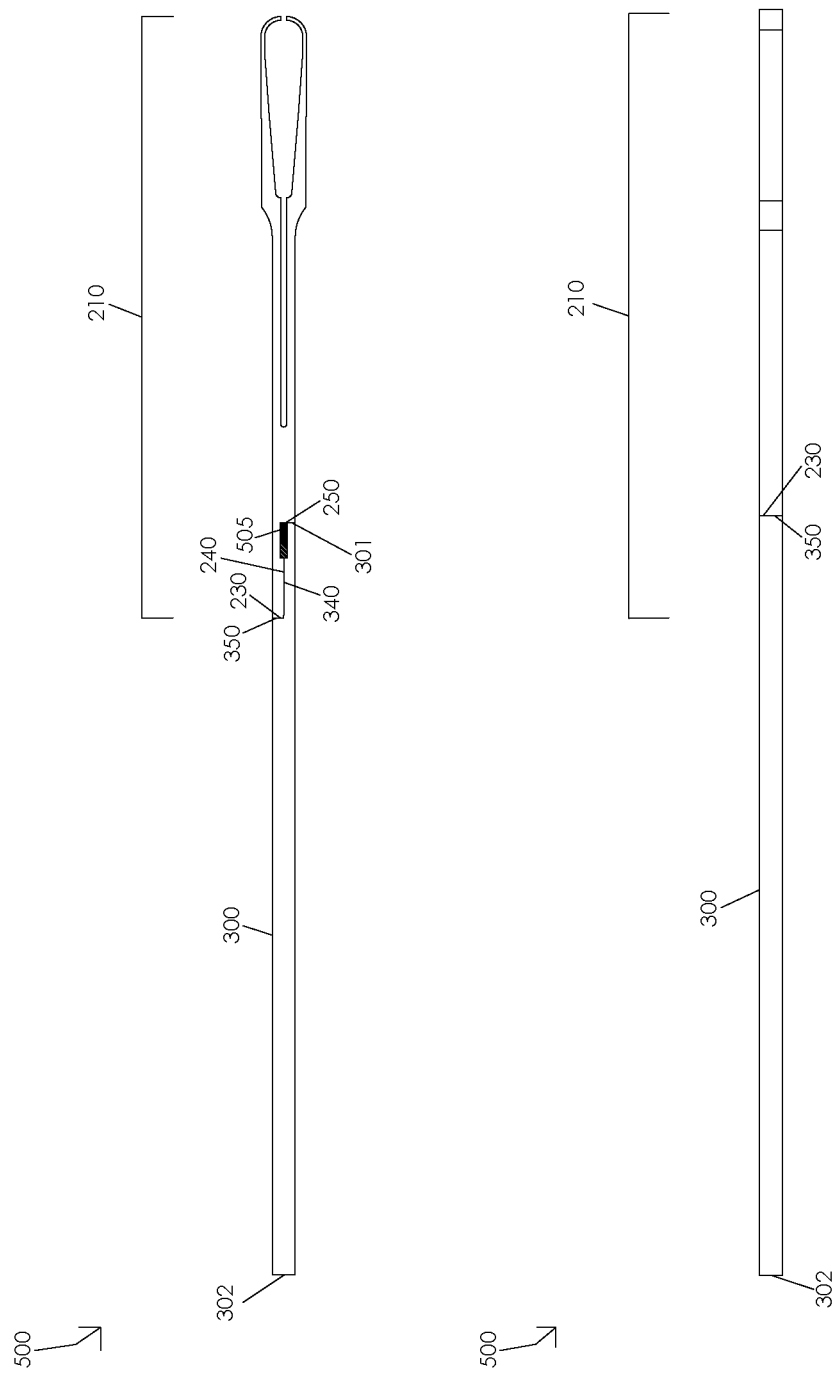

FIGS. 5A, 5B, 5C, and 5D are schematic diagrams illustrating an assembled blank 500. FIG. 5A illustrates a top view and a side view of an assembled blank 500. In one or more embodiments, assembled blank 500 may comprise a step blank base 300 fixed to a closed step blank tip 210. Illustratively, blank base shoulder interface 230 may be fixed to blank base shoulder 350. In one or more embodiments, blank base interface 240 may be fixed to blank tip interface 340. Illustratively, blank tip shoulder 250 may be fixed to blank tip shoulder interface 301. In one or more embodiments, step blank base 300 may be fixed to closed step blank tip 210 wherein a first portion of step blank base 300 adjacent to a first portion of closed step blank tip 210 forms a first plane and a second portion of step blank base 300 adjacent to a second portion of closed step blank tip 210 forms a second plane and the first plane is perpendicular to the second plane, e.g., blank base shoulder interface 230 and blank base shoulder 350 may comprise a first plane and blank base interface 240 and blank tip interface 340 may comprise a second plane wherein the first plane is perpendicular to the second plane. Illustratively, blank base interface 240 and blank tip interface 340 may comprise a first plane and blank tip shoulder 250 and blank tip shoulder interface 301 may comprise a second plane wherein the first plane is perpendicular to the second plane. In one or more embodiments, step blank base 300 may be fixed to closed step blank tip 210 wherein a first portion of step blank base 300 adjacent to a first portion of closed step blank tip 210 forms a first plane and a second portion of step blank base 300 adjacent to a second portion of closed step blank tip 210 forms a second plane and the first plane is parallel to the second plane, e.g., blank base shoulder interface 230 and blank base shoulder 350 may comprise a first plane and blank tip shoulder 250 and blank tip shoulder interface 301 may comprise a second plane wherein the first plane is parallel to the second plane. Illustratively, step blank base 300 may be fixed to closed step blank tip 210 wherein a first portion of step blank base 300 adjacent to a first portion of closed step blank tip 210 forms a first plane, a second portion of step blank base 300 adjacent to a second portion of closed step blank tip 210 forms a second plane, and a third portion of step blank base 300 adjacent to a third portion of closed step blank tip 210 forms a third plane and the first plane is parallel to the second plane and the third plane is perpendicular to the first plane and the second plane, e.g., blank base should interface 230 and blank base shoulder 350 may comprise a first plane, blank tip shoulder 250 and blank tip shoulder interface 301 may comprise a second plane, and blank base interface 240 and blank tip interface 340 may comprise a third plane wherein the first plane is parallel to the second plane and the third plane is perpendicular to the first plane and the second plane.

In one or more embodiments, step blank base 300 may be fixed to closed step blank tip 210 by an adhesive or any suitable fixation means, e.g., step blank base 300 may be fixed to closed step blank tip 210 by a press fit. Illustratively, step blank base 300 may be fixed to closed step blank tip 210 by a weld 505, e.g., step blank base 300 may be fixed to closed step blank tip 210 by a laser weld 505. Illustratively, step blank base 300 and closed step blank tip 210 may be welded together by a laser with an operating voltage set in a range of 190 to 210 Volts, e.g., step blank base 300 and closed step blank tip 210 may be welded together by a laser with an operating voltage set at 202 Volts. In one or more embodiments, step blank base 300 and closed step blank tip 210 may be welded together by a laser with an operating voltage set at less than 190 Volts or greater than 210 Volts. Illustratively, step blank base 300 and closed step blank tip 210 may be welded together by a laser with a pulse duration in a range of 0.5 to 2.5 milliseconds, e.g., step blank base 300 and closed step blank tip 210 may be welded together by a laser with a pulse duration of 1.7 milliseconds. In one or more embodiments, step blank base 300 and closed step blank tip 210 may be welded together by a laser with a pulse duration of less than 0.5 milliseconds or greater than 2.5 milliseconds. Illustratively, step blank base 300 and closed step blank tip 210 may be welded together by a laser with a frequency in a range of 1.0 to 5.0 Hz, e.g., step blank base 300 and closed step blank tip 210 may be welded together by a laser with a frequency of 2.5 Hz. In one or more embodiments, step blank base 300 and closed step blank tip 210 may be welded together by a laser with a frequency of less than 1.0 Hz or greater than 5.0 Hz. Illustratively, step blank base 300 and closed step blank tip 210 may be welded together by a laser having a spot diameter in a range of 0.10 to 0.50 millimeters, e.g., step blank base 300 and closed step blank tip 210 may be welded together by a laser having a spot diameter of 0.30 millimeters. In one or more embodiments, step blank base 300 and closed step blank tip 210 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

FIG. 5B illustrates a top view and a side view of an assembled blank 500. In one or more embodiments, assembled blank 500 may comprise a step blank base 300 fixed to an open step blank tip 211. Illustratively, blank base shoulder interface 230 may be fixed to blank base shoulder 350. In one or more embodiments, blank base interface 240 may be fixed to blank tip interface 340. Illustratively, blank tip shoulder 250 may be fixed to blank tip shoulder interface 301. In one or more embodiments, step blank base 300 may be fixed to open step blank tip 211 wherein a first portion of step blank base 300 adjacent to a first portion of open step blank tip 211 forms a first plane and a second portion of step blank base 300 adjacent to a second portion of open step blank tip 211 forms a second plane and the first plane is perpendicular to the second plane, e.g., blank base shoulder interface 230 and blank base shoulder 350 may comprise a first plane and blank base interface 240 and blank tip interface 340 may comprise a second plane wherein the first plane is perpendicular to the second plane. Illustratively, blank base interface 240 and blank tip interface 340 may comprise a first plane and blank tip shoulder 250 and blank tip shoulder interface 301 may comprise a second plane wherein the first plane is perpendicular to the second plane. In one or more embodiments, step blank base 300 may be fixed to open step blank tip 211 wherein a first portion of step blank base 300 adjacent to a first portion of open step blank tip 211 forms a first plane and a second portion of step blank base 300 adjacent to a second portion of open step blank tip 211 forms a second plane and the first plane is parallel to the second plane, e.g., blank base shoulder interface 230 and blank base shoulder 350 may comprise a first plane and blank tip shoulder 250 and blank tip shoulder interface 301 may comprise a second plane wherein the first plane is parallel to the second plane. Illustratively, step blank base 300 may be fixed to open step blank tip 211 wherein a first portion of step blank base 300 adjacent to a first portion of open step blank tip 211 forms a first plane, a second portion of step blank base 300 adjacent to a second portion of open step blank tip 211 forms a second plane, and a third portion of step blank base 300 adjacent to a third portion of open step blank tip 211 forms a third plane and the first plane is parallel to the second plane and the third plane is perpendicular to the first plane and the second plane, e.g., blank base should interface 230 and blank base shoulder 350 may comprise a first plane, blank tip shoulder 250 and blank tip shoulder interface 301 may comprise a second plane, and blank base interface 240 and blank tip interface 340 may comprise a third plane wherein the first plane is parallel to the second plane and the third plane is perpendicular to the first plane and the second plane.

In one or more embodiments, step blank base 300 may be fixed to open step blank tip 211 by an adhesive or any suitable fixation means, e.g., step blank base 300 may be fixed to open step blank tip 211 by a press fit. Illustratively, step blank base 300 may be fixed to open step blank tip 211 by a weld 505, e.g., step blank base 300 may be fixed to open step blank tip 211 by a laser weld 505. Illustratively, step blank base 300 and open step blank tip 211 may be welded together by a laser with an operating voltage set in a range of 190 to 210 Volts, e.g., step blank base 300 and open step blank tip 211 may be welded together by a laser with an operating voltage set at 202 Volts. In one or more embodiments, step blank base 300 and open step blank tip 211 may be welded together by a laser with an operating voltage set at less than 190 Volts or greater than 210 Volts. Illustratively, step blank base 300 and open step blank tip 211 may be welded together by a laser with a pulse duration in a range of 0.5 to 2.5 milliseconds, e.g., step blank base 300 and open step blank tip 211 may be welded together by a laser with a pulse duration of 1.7 milliseconds. In one or more embodiments, step blank base 300 and open step blank tip 211 may be welded together by a laser with a pulse duration of less than 0.5 milliseconds or greater than 2.5 milliseconds. Illustratively, step blank base 300 and open step blank tip 211 may be welded together by a laser with a frequency in a range of 1.0 to 5.0 Hz, e.g., step blank base 300 and open step blank tip 211 may be welded together by a laser with a frequency of 2.5 Hz. In one or more embodiments, step blank base 300 and open step blank tip 211 may be welded together by a laser with a frequency of less than 1.0 Hz or greater than 5.0 Hz. Illustratively, step blank base 300 and open step blank tip 211 may be welded together by a laser having a spot diameter in a range of 0.10 to 0.50 millimeters, e.g., step blank base 300 and open step blank tip 211 may be welded together by a laser having a spot diameter of 0.30 millimeters. In one or more embodiments, step blank base 300 and open step blank tip 211 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld

505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

FIG. 5C illustrates a top view and a side view of an assembled blank 500. In one or more embodiments, assembled blank 500 may comprise a blunt blank base 305 fixed to a closed blunt blank tip 212. Illustratively, blunt blank base interface 260 may be fixed to blunt blank tip interface 360. In one or more embodiments, blunt blank base 305 may be fixed to closed blunt blank tip 212 by an adhesive or any suitable fixation means, e.g., blunt blank base 305 may be fixed to closed blunt blank tip 212 by a press fit. Illustratively, blunt blank base 305 may be fixed to closed blunt blank tip 212 by a weld 505, e.g., blunt blank base 305 may be fixed to closed blunt blank tip 212 by a laser weld 505. Illustratively, blunt blank base 305 and closed blunt blank tip 212 may be welded together by a laser with an operating voltage set in a range of 190 to 210 Volts, e.g., blunt blank base 305 and closed blunt blank tip 212 may be welded together by a laser with an operating voltage set at 202 Volts. In one or more embodiments, blunt blank base 305 and closed blunt blank tip 212 may be welded together by a laser with an operating voltage set at less than 190 Volts or greater than 210 Volts. Illustratively, blunt blank base 305 and closed blunt blank tip 212 may be welded together by a laser with a pulse duration in a range of 0.5 to 2.5 milliseconds, e.g., blunt blank base 305 and closed blunt blank tip 212 may be welded together by a laser with a pulse duration of 1.7 milliseconds. In one or more embodiments, blunt blank base 305 and closed blunt blank tip 212 may be welded together by a laser with a pulse duration of less than 0.5 milliseconds or greater than 2.5 milliseconds. Illustratively, blunt blank base 305 and closed blunt blank tip 212 may be welded together by a laser with a frequency in a range of 1.0 to 5.0 Hz, e.g., blunt blank base 305 and closed blunt blank tip 212 may be welded together by a laser with a frequency of 2.5 Hz. In one or more embodiments, blunt blank base 305 and closed blunt blank tip 212 may be welded together by a laser with a frequency of less than 1.0 Hz or greater than 5.0 Hz. Illustratively, blunt blank base 305 and closed blunt blank tip 212 may be welded together by a laser having a spot diameter in a range of 0.10 to 0.50 millimeters, e.g., blunt blank base 305 and closed blunt blank tip 212 may be welded together by a laser having a spot diameter of 0.30 millimeters. In one or more embodiments, blunt blank base 305 and closed blunt blank tip 212 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 5D:
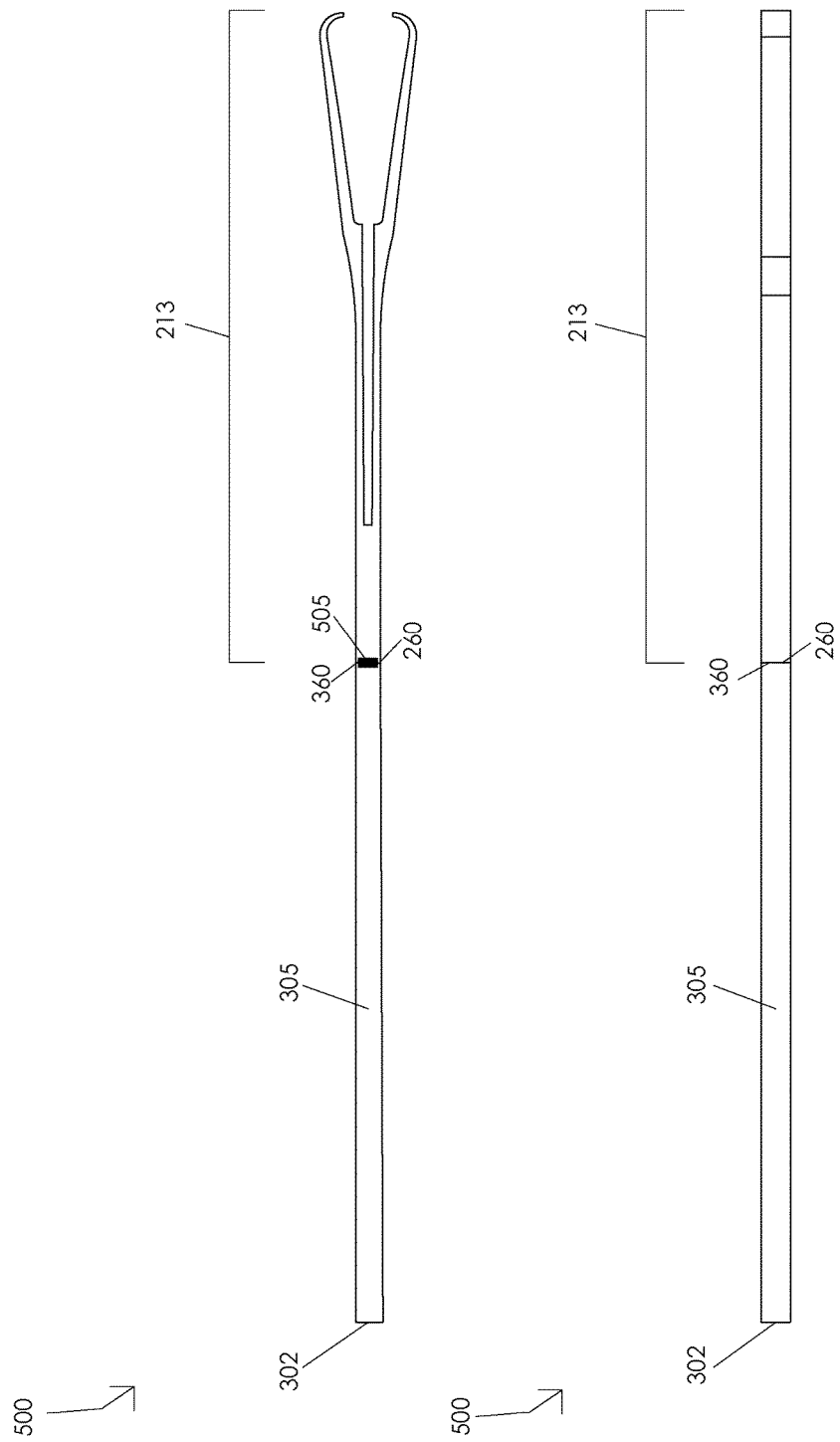

FIG. 5D illustrates a top view and a side view of an assembled blank 500. In one or more embodiments, assembled blank 500 may comprise a blunt blank base 305 fixed to an open blunt blank tip 213. Illustratively, blunt blank base interface 260 may be fixed to blunt blank tip interface 360. In one or more embodiments, blunt blank base 305 may be fixed to closed blunt blank tip 212 by an adhesive or any suitable fixation means, e.g., blunt blank base 305 may be fixed to open blunt blank tip 213 by a press fit. Illustratively, blunt blank base 305 may be fixed to open blunt blank tip 213 by a weld 505, e.g., blunt blank base 305 may be fixed to open blunt blank tip 213 by a laser weld 505. Illustratively, blunt blank base 305 and open blunt blank tip 213 may be welded together by a laser with an operating voltage set in a range of 190 to 210 Volts, e.g., blunt blank base 305 and open blunt blank tip 213 may be welded together by a laser with an operating voltage set at 202 Volts. In one or more embodiments, blunt blank base 305 and open blunt blank tip 213 may be welded together by a laser with an operating voltage set at less than 190 Volts or greater than 210 Volts. Illustratively, blunt blank base 305 and open blunt blank tip 213 may be welded together by a laser with a pulse duration in a range of 0.5 to 2.5 milliseconds, e.g., blunt blank base 305 and open blunt blank tip 213 may be welded together by a laser with a pulse duration of 1.7 milliseconds. In one or more embodiments, blunt blank base 305 and open blunt blank tip 213 may be welded together by a laser with a pulse duration of less than 0.5 milliseconds or greater than 2.5 milliseconds. Illustratively, blunt blank base 305 and open blunt blank tip 213 may be welded together by a laser with a frequency in a range of 1.0 to 5.0 Hz, e.g., blunt blank base 305 and open blunt blank tip 213 may be welded together by a laser with a frequency of 2.5 Hz. In one or more embodiments, blunt blank base 305 and open blunt blank tip 213 may be welded together by a laser with a frequency of less than 1.0 Hz or greater than 5.0 Hz. Illustratively, blunt blank base 305 and open blunt blank tip 213 may be welded together by a laser having a spot diameter in a range of 0.10 to 0.50 millimeters, e.g., blunt blank base 305 and open blunt blank tip 213 may be welded together by a laser having a spot diameter of 0.30 millimeters. In one or more embodiments, blunt blank base 305 and open blunt blank tip 213 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 6:
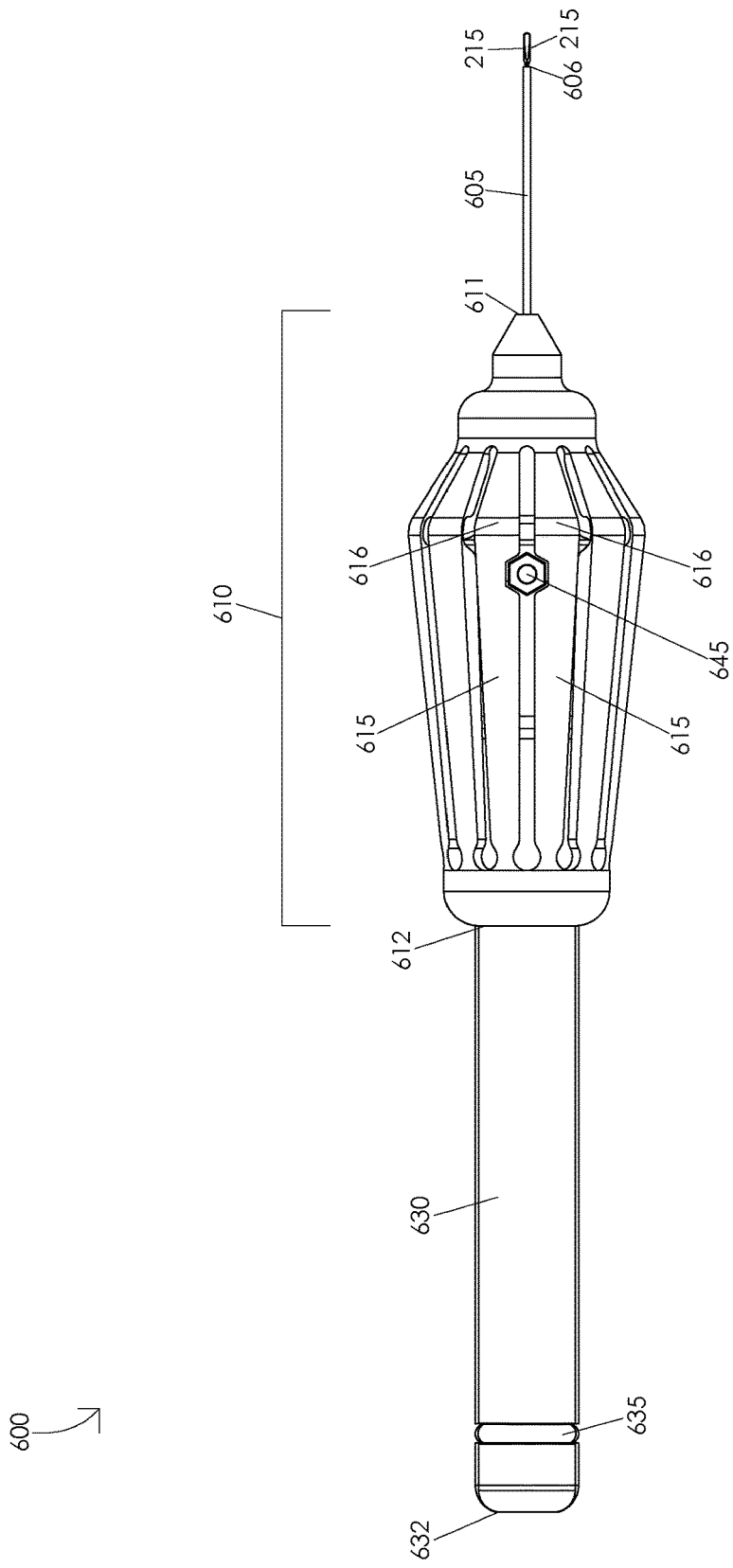
FIG. 6 is a schematic diagram illustrating a microsurgical instrument.

FIG. 6 is a schematic diagram illustrating a microsurgical instrument 600. In one or more embodiments, microsurgical instrument 600 may comprises a hypodermic tube 605, an actuation structure 610, and an end stick 630. Illustratively, actuation structure 610 may comprise an actuation structure distal end 611, an actuation structure proximal end 612, and a plurality of actuation arms 615. In one or more embodiments, each actuation arm 615 of a plurality of actuation arms 615 may comprise an extension mechanism 616.

Illustratively, actuation structure distal end 611 may extend a decompressed distance from actuation structure proximal end 612, e.g., when actuation structure 610 comprises a decompressed actuation structure 610. In one or more embodiments, a decompressed distance may be in a range of 1.6 to 3.0 inches, e.g., a decompressed distance may be 2.25 inches. Illustratively, a decompressed distance may be less than 1.6 inches or greater than 3.0 inches. In one or more embodiments, actuation structure 610 may be manufactured from any suitable material, e.g., polymers, metals, metal alloys, etc., or from any combination of suitable materials. Illustratively, actuation structure 610 may be manufactured from a shape memory material. In one or more embodiments, actuation structure 610 may be manufactured using a selective laser sintering machine. Illustratively, actuation structure 610 may be manufactured by additive manufacturing or 3D printing. In one or more embodiments, actuation structure 610 may be manufactured from a material suitable for sterilization by a medical autoclave. Illustratively, actuation structure 610 may be manufactured from a material, e.g., Nylon, configured to withstand exposure to temperatures, pressures, and ambient conditions present in a medical autoclave without degradation. For example, actuation structure 610 may be configured to function normally after exposure in a temperature 250° F. for 15 minutes at an atmospheric pres-sure of 15 psi. In one or more embodiments, actuation structure 610 may be configured to be used in a surgical procedure and then sterilized by a medical autoclave at least three times. Illustratively, actuation structure 610 may be configured to be used in a surgical procedure and then sterilized by a medical autoclave more than three times.

In one or more embodiments, actuation structure 610 may have a density in a range of 0.02 to 0.06 pounds per cubic inch, e.g., actuation structure 610 may have a density of 0.042 pounds per cubic inch. Illustratively, actuation structure 610 may have a density less than 0.02 pounds per cubic inch or greater than 0.06 pounds per cubic inch. In one or more embodiments, actuation structure 610 may have a mass in a range of 0.005 to 0.025 pounds, e.g., actuation structure 610 may have a mass of 0.015 pounds. Illustratively, actuation structure 610 may have a mass less than 0.005 pounds or greater than 0.025 pounds. In one or more embodiments, actuation structure 610 may have a volume in a range of 0.2 to 0.5 cubic inches, e.g., actuation structure 610 may have a volume of 0.359 cubic inches. Illustratively, actuation structure 610 may have a volume less than 0.2 cubic inches or greater than 0.5 cubic inches. In one or more embodiments, actuation structure 610 may have a surface area in a range of 7.5 to 13.0 square inches, e.g., actuation structure 610 may have a surface area of 10.8 square inches. Illustratively, actuation structure 610 may have a surface area less than 7.5 square inches or greater than 13.0 square inches.

In one or more embodiments, actuation structure 610 may be configured to project actuation structure distal end 611 a first distance from actuation structure proximal end 612, e.g., when actuation structure 610 is fully decompressed. Illustratively, actuation structure 610 may comprise a shape memory material configured to project actuation structure distal end 611 a second distance from actuation structure proximal end 612, e.g., when actuation structure 610 is fully compressed. In one or more embodiments, the second distance from actuation structure proximal end 612 may be greater than the first distance from actuation structure proximal end 612. Illustratively, a compression of actuation structure 610 may be configured to gradually extend actuation structure distal end 611 relative to actuation structure proximal end 612. In one or more embodiments, actuation structure distal end 611 may extend a compressed distance from actuation structure proximal end 612, e.g., when actuation structure 610 comprises a compressed actuation structure 610. Illustratively, a compressed distance may be a distance in a range of 1.6 to 3.0 inches, e.g., a compressed distance may be 2.29 inches. In one or more embodiments, a compressed distance may be less than 1.6 inches or greater than 3.0 inches. Illustratively, a compressed distance may be in a range of 0.02 to 0.05 inches greater than a decompressed distance. In one or more embodiments, a compressed distance may be less than 0.02 inches greater than a decompressed distance. Illustratively, a compressed distance may be more than 0.05 inches greater than a decompressed distance. In one or more embodiments, a compressed distance may be in a range of 1.0 to 2.0 percent greater than a decompressed distance. Illustratively, a compressed distance may be less than 1.0 percent greater than a decompressed distance. In one or more embodiments, a compressed distance may be more than 2.0 percent greater than a decompressed distance.

Illustratively, actuation structure 610 may be compressed by an application of a force, e.g., a compressive force, to a portion of actuation structure 610. In one or more embodiments, an application of a compressive force in a range of 100 to 300 grams may be configured to compress actuation structure 610, e.g., an application of a compressive force of 200 grams may be configured to compress actuation structure 610. Illustratively, an application of a compressive force of less than 100 grams or greater than 300 grams may be configured to compress actuation structure 610. In one or more embodiments, actuation structure 610 may be compressed by an application of one or more compressive forces at one or more locations around an outer perimeter of actuation structure 610. Illustratively, the one or more locations may comprise any particular locations of a plurality of locations around an outer perimeter of actuation structure 610. For example, a surgeon may compress actuation structure 610 by squeezing actuation structure 610. Illustratively, a surgeon may compress actuation structure 610 by squeezing actuation structure 610 at any particular location of a plurality of locations around an outer perimeter of actuation structure 610. In one or more embodiments, a surgeon may compress actuation structure 610 by applying a force to a portion of actuation structure 610, e.g., when actuation structure 610 is in a first rotational orientation. Illustratively, the surgeon may then rotate actuation structure 610 and compress actuation structure 610 by applying a force to a portion of actuation structure 610, e.g., when actuation structure 610 is in a second rotational orientation. In one or more embodiments, the surgeon may then rotate actuation structure 610 and compress actuation structure 610 by applying a force to a portion of actuation structure 610, e.g., when actuation structure 610 is in a third rotational orientation. Illustratively, a surgeon may compress actuation structure 610 by applying a force to a portion of actuation structure 610, e.g., when actuation structure 610 is in any rotational orientation.

In one or more embodiments, actuation structure 610 may be compressed by an application of a compressive force to any one or more actuation arms 615 of a plurality of actuation arms 615. Illustratively, each actuation arm 615 may be connected to one or more actuation arms 615 of a plurality of actuation arms 615 wherein an actuation of a particular actuation arm 615 may be configured to actuate every actuation arm 615 of a plurality of actuation arms 615.

In one or more embodiments, one or more actuation arms 615 may be configured to actuate in pairs or groups. For example, an actuation of a first actuation arm 615 may be configured to actuate a second actuation arm 615. Illustratively, a compression of actuation structure 610, e.g., due to an application of a force to a portion of actuation structure 610, may be configured to expand an extension mechanism 616 of a particular actuation arm 110. In one or more embodiments, an expansion of an extension mechanism 616 of a particular actuation arm 615 may be configured to increase a distance between a distal end and a proximal end of the particular actuation arm 615. Illustratively, an expansion of an extension mechanism 616 of a particular actuation arm 615 may be configured to expand an extension mechanism 616 of every actuation arm 615 of a plurality of actuation arms 615. In one or more embodiments, an expansion of an extension mechanism 616 of every actuation arm 615 of a plurality of actuation arms 615 may be configured to increase a distance between actuation structure distal end 611 and actuation structure proximal end 612. Illustratively, a decompression of actuation structure 610, e.g., due to a reduction of a force applied to a portion of actuation structure 610, may be configured to collapse an extension mechanism 616 of a particular actuation arm 615. In one or more embodiments, a collapse of an extension mechanism 616 of a particular actuation arm 615 may be configured to decrease a distance between a distal end and a proximal end of the particular actuation arm 615. Illustratively, a collapse of an extension mechanism 616 of a particular actuation arm 615 may be configured to collapse an extension mechanism 616 of every actuation arm 615 of a plurality of actuation arms 615. In one or more embodiments, a collapse of an extension mechanism 616 of every actuation arm 615 of a plurality of actuation arms 615 may be configured to decrease a distance between actuation structure distal end 611 and actuation structure proximal end 612.

Illustratively, end stick 630 may comprise an end stick distal end, an end stick proximal end 632, and an identification marker 635. In one or more embodiments, end stick 630 may be fixed to a portion of actuation structure 610, e.g., a portion of end stick 630 may be disposed within actuation structure 610. Illustratively, identification marker 635 may be configured to convey information about microsurgical instrument 600, e.g., identification marker 635 may comprise a color configured to correspond to a particular assembled blank 500. In one or more embodiments, identification marker 635 may comprise a color configured to correspond to a particular size of assembled blank 500. Illustratively, hypodermic tube 605 may comprise a hypodermic tube distal end 606 and a hypodermic tube proximal end. In one or more embodiments, hypodermic tube 605 may be fixed to actuation structure 610, e.g., a portion of hypodermic tube 605 may be disposed within actuation structure 610. Illustratively, assembled blank 500 may be disposed within hypodermic tube 605 and actuation structure 610, e.g., assembled blank 500 may be disposed within hypodermic tube 605 wherein first forceps jaw distal end 216 extends out from hypodermic tube distal end 606 and second forceps jaw distal end 216 extends out from hypodermic tube distal end 606. In one or more embodiments, assembled blank 500 may be fixed within actuation structure 610, e.g., fixation mechanism 645 may be configured to fix a portion of assembled blank 500 within actuation structure 610. For example, fixation mechanism 645 may comprise a setscrew. Illustratively, a portion of assembled blank 500 may be fixed within actuation structure 610 by an adhesive or any suitable fixation means, e.g., a portion of assembled blank 500 may be fixed within actuation structure 610 by a friction fit, a weld, a tie, etc.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument tip, the teachings of the present invention are equally suitable to any systems where the functionality may be employed. Therefore, it is the object of the appended claims to cover all such variations and modifications as come within the true spirit and scope of the invention.

What is claimed is:

1. A method of manufacturing a microsurgical instrument tip comprising:
    disposing a first flat stock in a plane perpendicular to a tool electrode of an electrical discharge machine wherein the first flat stock has a first flat stock distal end, a first flat stock proximal end, a first flat stock dorsal end, and a first flat stock ventral end and wherein the first flat stock has a flat stock thickness greater than 0.005 inches;
    actuating the first flat stock relative to the tool electrode;
    cutting predetermined patterns into the first flat stock to form a plurality of blank tips;
    separating the plurality of blank tips cut from the first flat stock, and
    welding a first blank base to a first blank tip of the plurality of separated blank tips;
    wherein each blank tip of the plurality of blank tips has a first forceps jaw with a first forceps jaw distal end and a first forceps jaw proximal end, a second forceps jaw with a second forceps jaw distal end and a second forceps jaw proximal end, a blank tip aperture and a blank base interface,
    wherein the first forceps jaw distal end is separated from the second forceps jaw distal end by a jaw separation distance; and
    wherein welding the first blank base to the first blank tip of the plurality of separated blank tips includes welding the first blank base to the blank base interface of the first blank tip.

2. The method of claim 1 further comprising:
    disposing the first blank base in a hypodermic tube and an actuation structure of a microsurgical instrument.

3. The method of claim 2 wherein the actuation structure is manufactured by additive manufacturing.

4. The method of claim 2 wherein the actuation structure is manufactured by 3D printing.

5. The method of claim 2 wherein the actuation structure is manufactured from nylon.

6. The method of claim 2 wherein the actuation structure has a density in a range of 0.02 to 0.06 pounds per cubic inch.

7. The method of claim 2 wherein the actuation structure has a mass in a range of 0.005 to 0.025 pounds.

8. The method of claim 2 wherein the actuation structure has a volume in a range of 0.2 to 0.5 cubic inches.

9. The method of claim 2 wherein the actuation structure has a surface area in a range of 7.5 to 13.0 square inches.

10. The method of claim 2 further comprising:
    compressing the actuation structure.

11. The method of claim 2 further comprising:
decompressing the actuation structure.

12. The method of claim 1 wherein the first flat stock is manufactured from stainless steel.

13. The method of claim 12 wherein the first flat stock is manufactured from 17-7 PH stainless steel condition C.

14. The method of claim 1 wherein the first flat stock thickness is less than 0.013 inches.

15. The method of claim 1 wherein the jaw separation distance of the first blank tip is in a range of 0.001 to 0.005 inches.

16. The method of claim 1 wherein the jaw separation distance of the first blank tip is in a range of 0.01 to 0.05 inches.

17. The method of claim 1 wherein the first flat stock thickness is in a range of 0.007 to 0.009 inches.

18. The method of claim 1 wherein the first flat stock thickness is in a range of 0.011 inches to 0.013 inches.

19. The method of claim 1 wherein the first flat stock thickness is greater than 0.013 inches.

\* \* \* \* \*